US 6,358,237 B1

(12) United States Patent
Paukovits et al.

(10) Patent No.: US 6,358,237 B1
(45) Date of Patent: Mar. 19, 2002

(54) METHODS AND APPARATUS FOR DELIVERING FLUIDS TO A PATIENT

(75) Inventors: Dorothy A. Paukovits, deceased, late of Bethlehem; by Edward J. Paukovits, Jr. legal representative, Hummelstown; Janet Hoffner, Halifax, all of PA (US); Paul Caron, Laurel; Andrew Leonard, Sykesville, both of MD (US)

(73) Assignee: Assistive Technology Products, Inc., Hummelstown, PA (US)

( * ) Notice: Subject to any disclaimer, the term of this patent is extended or adjusted under 35 U.S.C. 154(b) by 0 days.

(21) Appl. No.: 09/233,282

(22) Filed: Jan. 19, 1999

(51) Int. Cl.[7] .............................................. A61M 31/00
(52) U.S. Cl. ........................ 604/516; 604/77; 604/151; 604/65
(58) Field of Search .......................... 604/151, 67, 131, 604/65, 500, 514, 516, 505, 118, 77–79

(56) References Cited

U.S. PATENT DOCUMENTS

| | | | | |
|---|---|---|---|---|
| 3,669,101 A | * | 6/1972 | Kleiner .......................... 128/66 |
| 4,370,983 A | | 2/1983 | Lichtenstein ................. 128/630 |
| 4,463,859 A | * | 8/1984 | Greene .......................... 215/11 |
| 4,950,254 A | * | 8/1990 | Andersen et al. ............ 604/247 |
| 4,966,580 A | * | 10/1990 | Turner et al. .................. 604/67 |
| 5,681,285 A | * | 10/1997 | Ford et al. .................... 604/151 |
| 5,772,635 A | * | 6/1998 | Dastur et al. ................. 604/131 |
| 5,795,317 A | | 8/1998 | Brierton et al. ................. 604/5 |
| 5,803,917 A | * | 9/1998 | Butterfield et al. ............ 604/67 |
| 5,814,015 A | * | 9/1998 | Gargano et al. ............... 604/67 |
| 5,830,235 A | | 11/1998 | Standley ..................... 606/234 |
| 5,975,897 A | | 11/1999 | Propp et al. ................... 433/91 |

* cited by examiner

Primary Examiner—Richard K. Seidel
Assistant Examiner—Jennifer Maynard
(74) Attorney, Agent, or Firm—Duane, Morris & Heckscher LLP

(57) ABSTRACT

A system for delivering fluids which includes a pump (such as a peristaltic pump for example), a pump cartridge, a fluid reservoir, and a variety of fluid dispensers, including oral fluid dispensers. By providing a number of oral fluid dispensers, the one best suited for the needs of a particular application can be selected. The pump cartridge and/or the fluid dispensers may be disposable. The operation of the pump may be controlled based, at least in part, on the type of fluid dispenser being used. Further, a selectable mode can be used to further control the operation of the pump. The amount of fluids delivered over given periods of time may be monitored such that a reminder (such as an audio and/or visual alarm for example) may be provided if too much or too little fluid is delivered (and presumably consumed). The thresholds for such alarm conditions may be set and modified by a user. Further, the state of the fluid delivery system itself, as well as trends in fluid delivery, may be monitored.

11 Claims, 36 Drawing Sheets

METHODS AND APPARATUS FOR DELIVERING FLUIDS TO A PATIENT

§1. BACKGROUND OF THE INVENTION

§1.1 Field of the Invention

The present invention concerns methods and apparatus for delivering fluids, and in particular, concerns delivering fluids via a variety of oral dispensers. Although it is expected that the present invention will be used primarily for maintaining the hydration and comfort of people, and the present invention will be described primarily in that context, other uses are also possible.

§1.2 Related Art

Maintaining a person's hydration and maximizing their comfort is an important aspect of maintaining their well-being. In extreme cases, people may need to be hydrated intravenously, by means of a peristaltic pump dosing fluids, via a tube and hollow needle, into the person's vein. In less extreme cases, people may drink directly from a cup, sip from a straw, or suck on frozen fluids, either unassisted, or with the assistance of a lay or professional caregiver. If possible, it is preferable to maintain a person's hydration by administering fluids orally, rather than intravenously, especially if the person is living in a home setting and/or has limited access to a full-time professional caregiver.

§2. SUMMARY OF THE INVENTION

Given the preference for oral hydration, which is less invasive than intravenous hydration, it is a goal of the present invention to overcome challenges to oral hydration. For example, a person may be too weak to lift and manipulate, or too unsteady to regulate, a cup filled with fluids. A person may "just want to be left alone" or may be forgetful and consume too little fluid without gentle reminders. Thus, one of the goals of the invention is to monitor a person's fluid intake and remind people to consume fluids if they have not consumed enough over a given time period. Finally, a person's mouth or throat may be sore or sensitive, either due to incisions, wounds, or swelling from surgery, blisters from radiation treatment or chemotherapy, or fungal or bacterial infections from a weakened immune system. Such circumstances may make it painful to even consume fluids orally. Thus, one of the goals of the present invention is to provide various oral fluid dispensers thereby allowing the person (or caregiver) to chose the most appropriate one. Some of the fluid dispensers of the present invention are extremely gentle and reduce the likelihood of aggravating wounds, infections, or blisters. All of the oral fluid dispensers of the present invention are designed to allow people to self regulate the amount of fluids they consume, and the rate at which they consume them (while reminding them if they have consumed too little, as discussed above).

In addition to the above goals, the present invention also seeks to permit bottles or containers of commercially purchased fluids to be used. To the extent that any parts need cleaning or sterilizing, such parts should be easy to clean or should be inexpensive and/or recyclable so that they are disposable.

The present invention provides a system for delivering fluids which includes a pump (such as a peristaltic pump for example), a pump cartridge, a fluid reservoir, and a variety of fluid dispensers, including oral fluid dispensers. Since a number of oral fluid dispensers are provided, the one best suited for the needs of a particular application can be selected. The pump cartridge and/or the fluid dispensers are disposable. The operation of the pump may be controlled based, at least in part, on the type of fluid dispenser being used. Further, a selectable mode can be used to further control the operation of the pump.

The present invention also provides methods and apparatus for monitoring the amount of fluids delivered over given periods of time. If too much or too little fluid is delivered (and presumably consumed), the present invention may provide a reminder (such as an audio and/or visual alarm for example). The thresholds for such alarm conditions may be set and modified by a user.

The present invention also provides methods and apparatus for monitoring the state of the fluid delivery system itself, and monitoring trends in fluid delivery.

§3. BRIEF DESCRIPTION OF THE DRAWINGS

Figures 4, 4A:
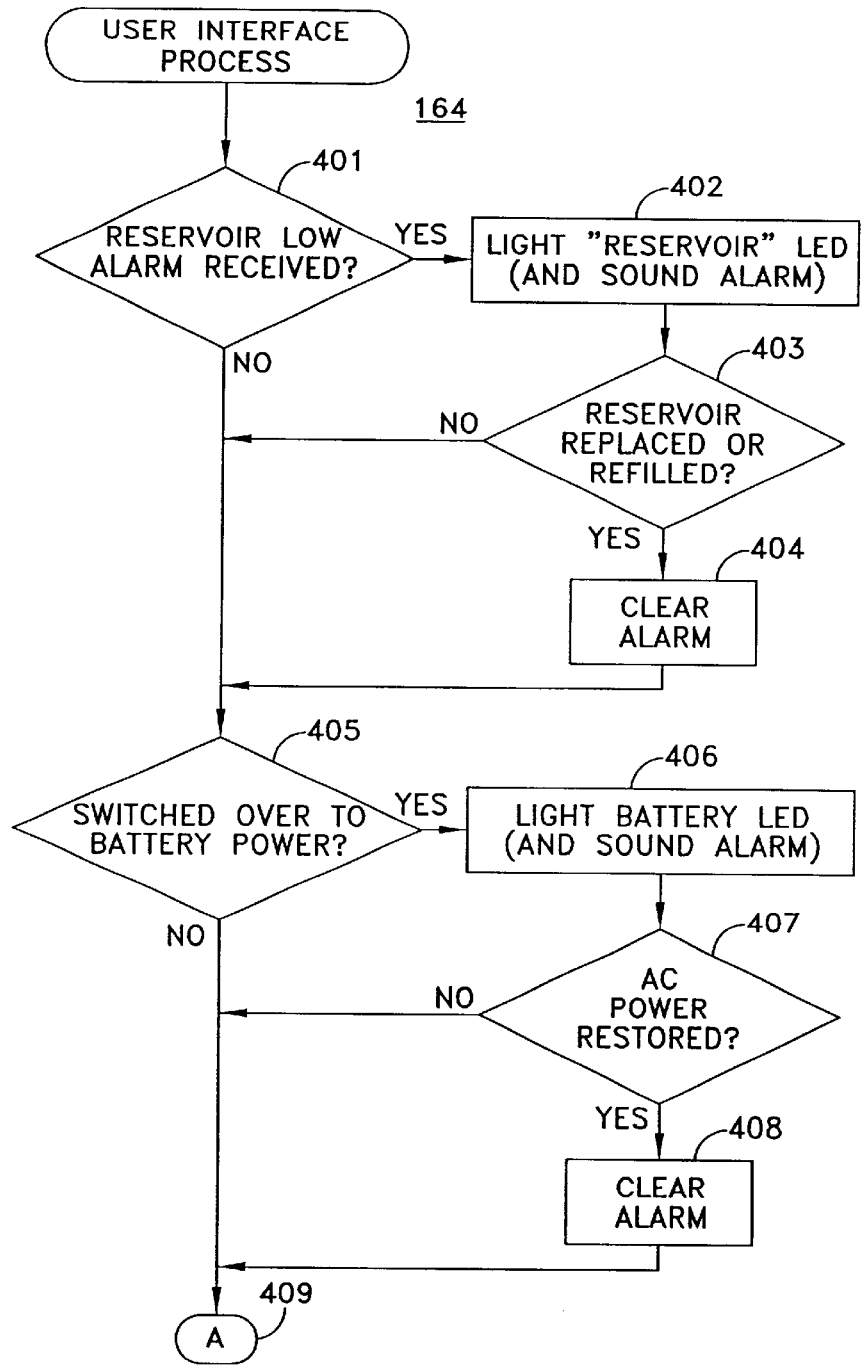
Figure 4B:
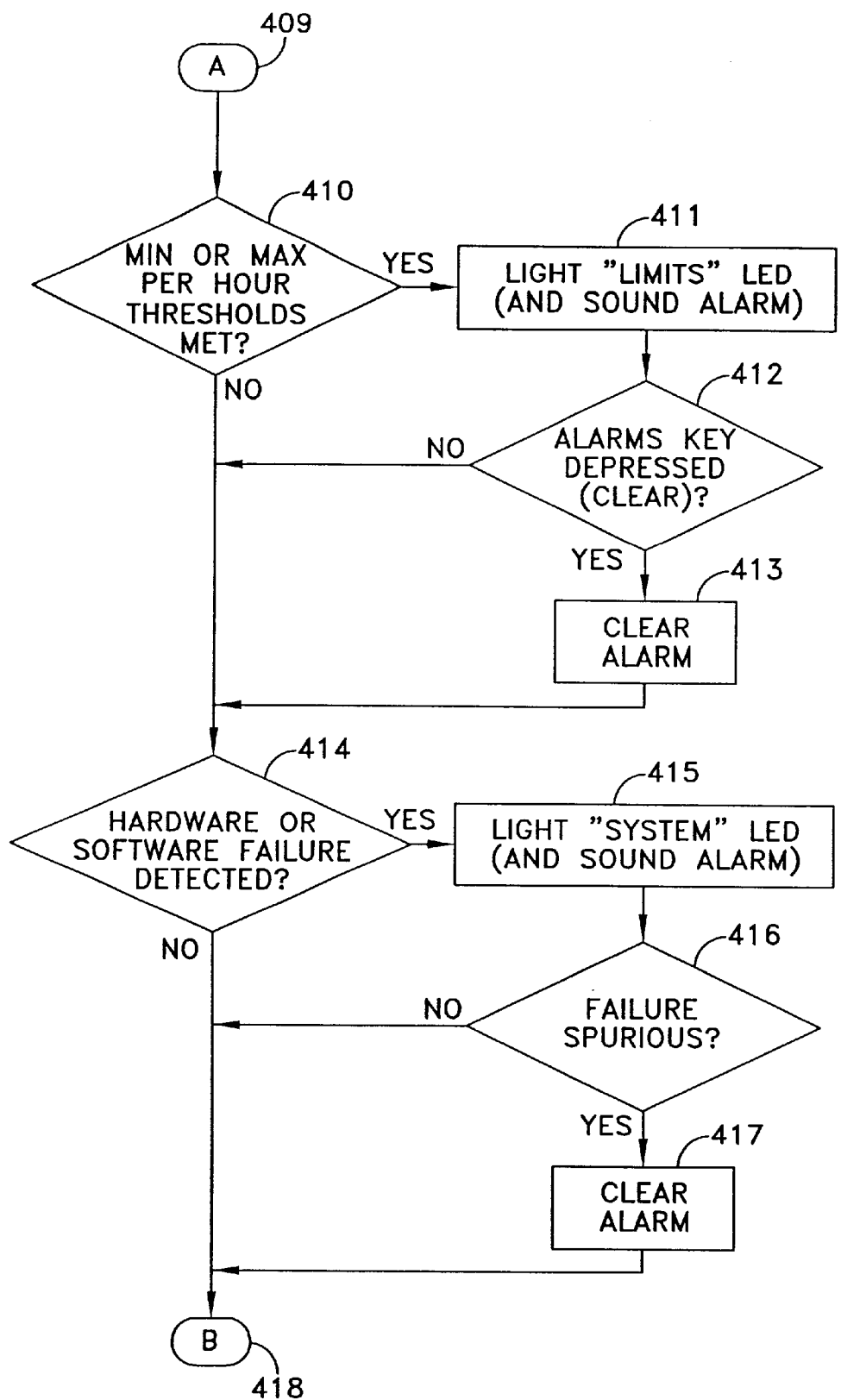
Figure 4C:
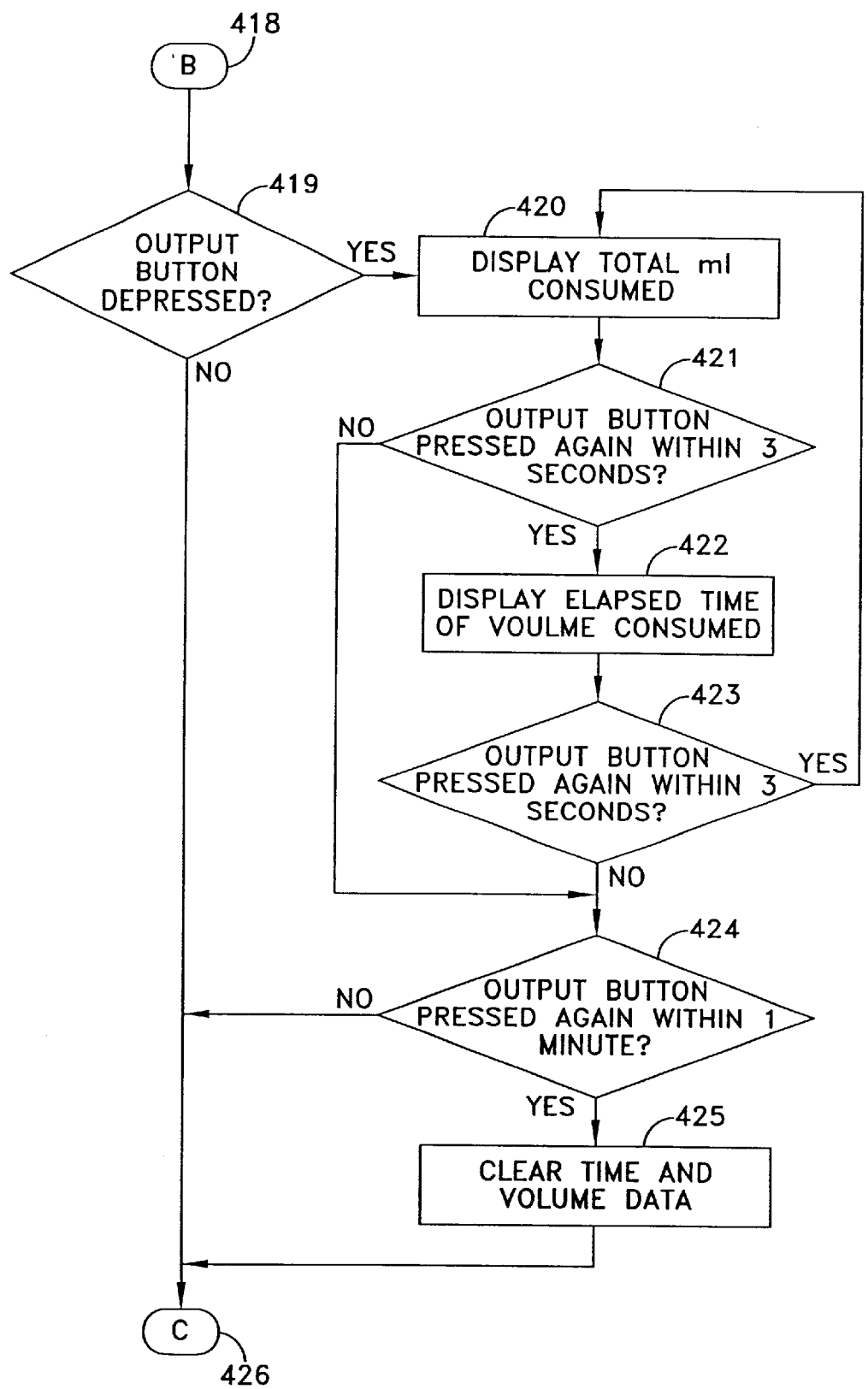
Figure 4D:
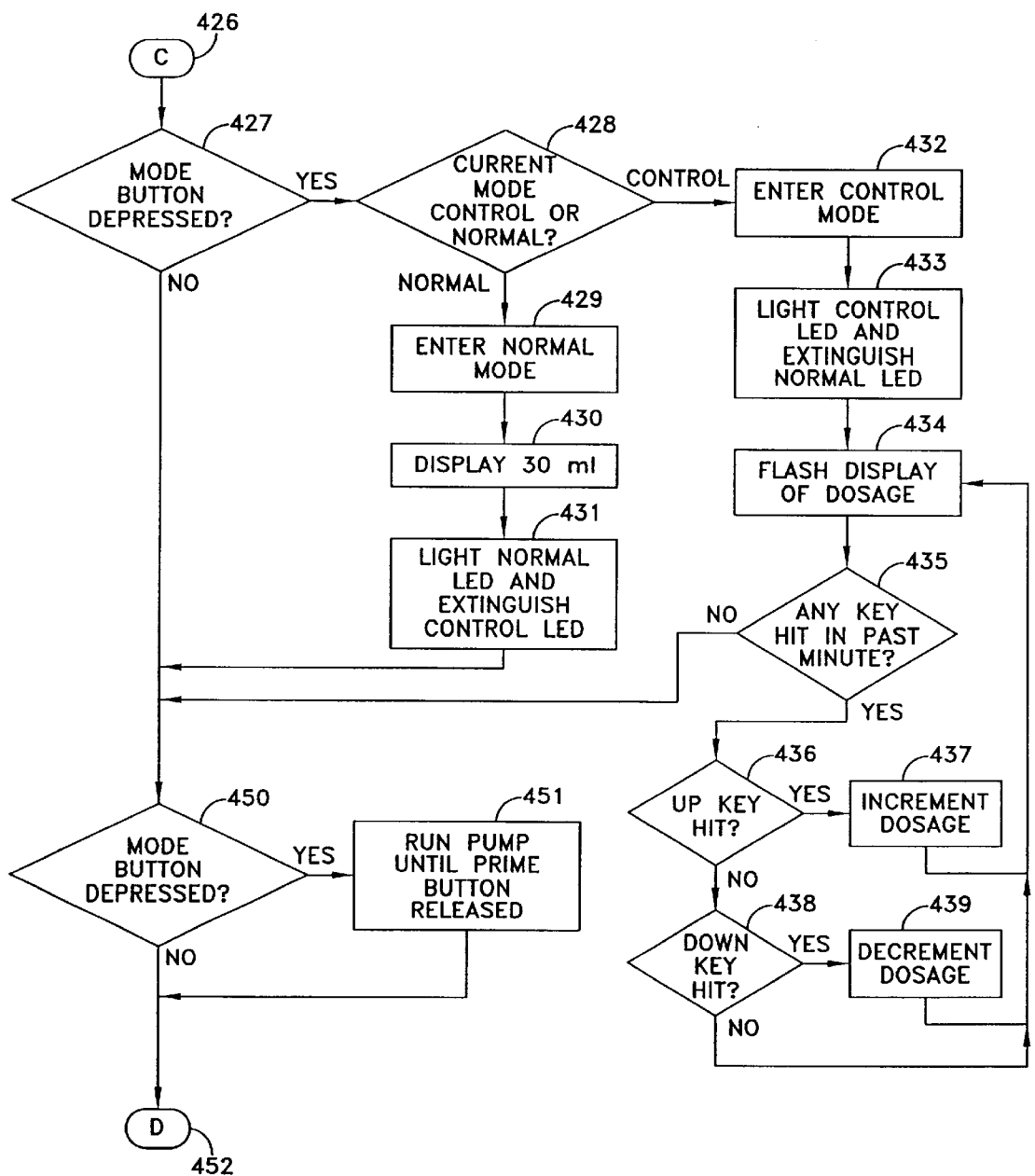
Figure 4E:
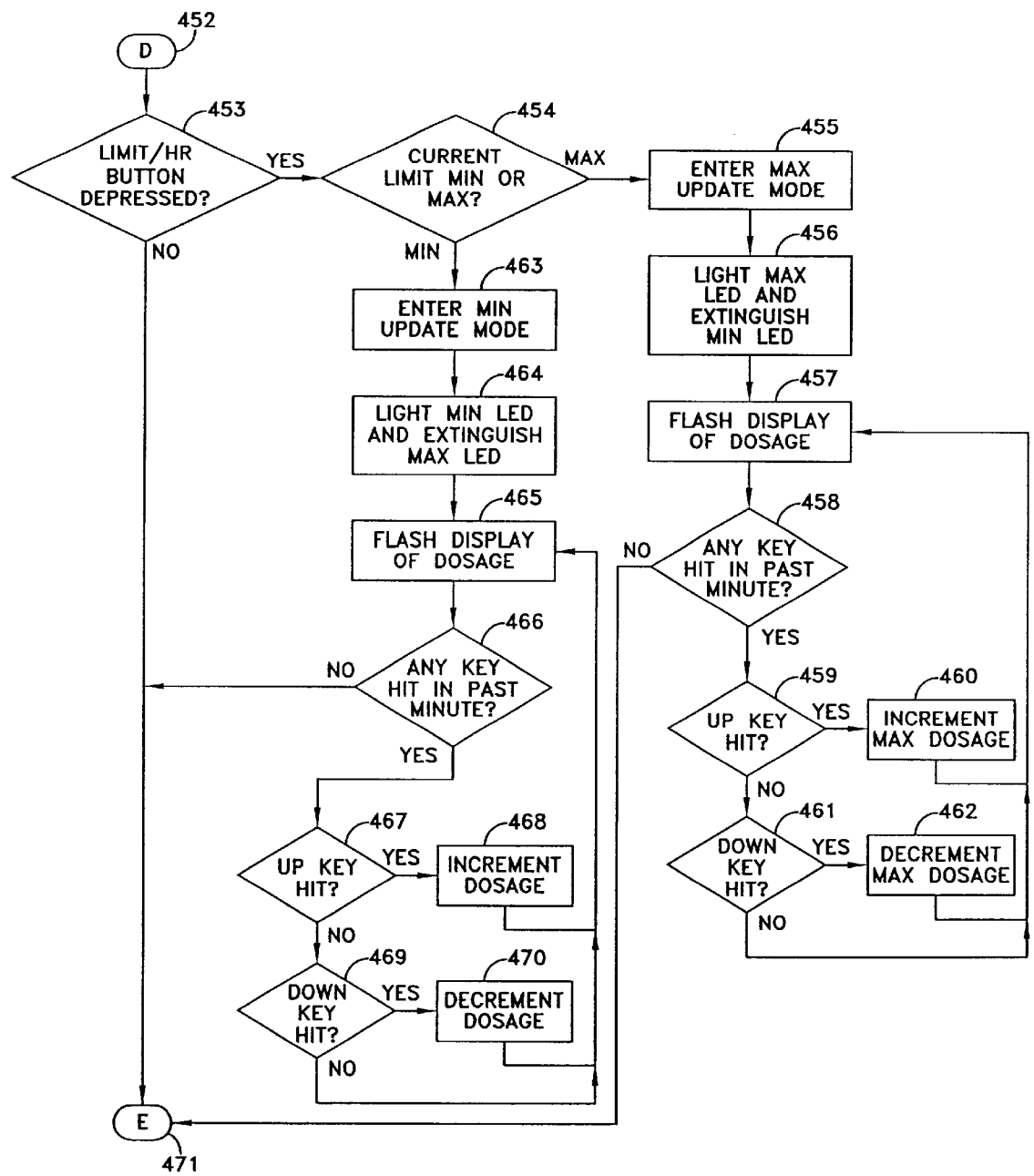
Figure 4F:
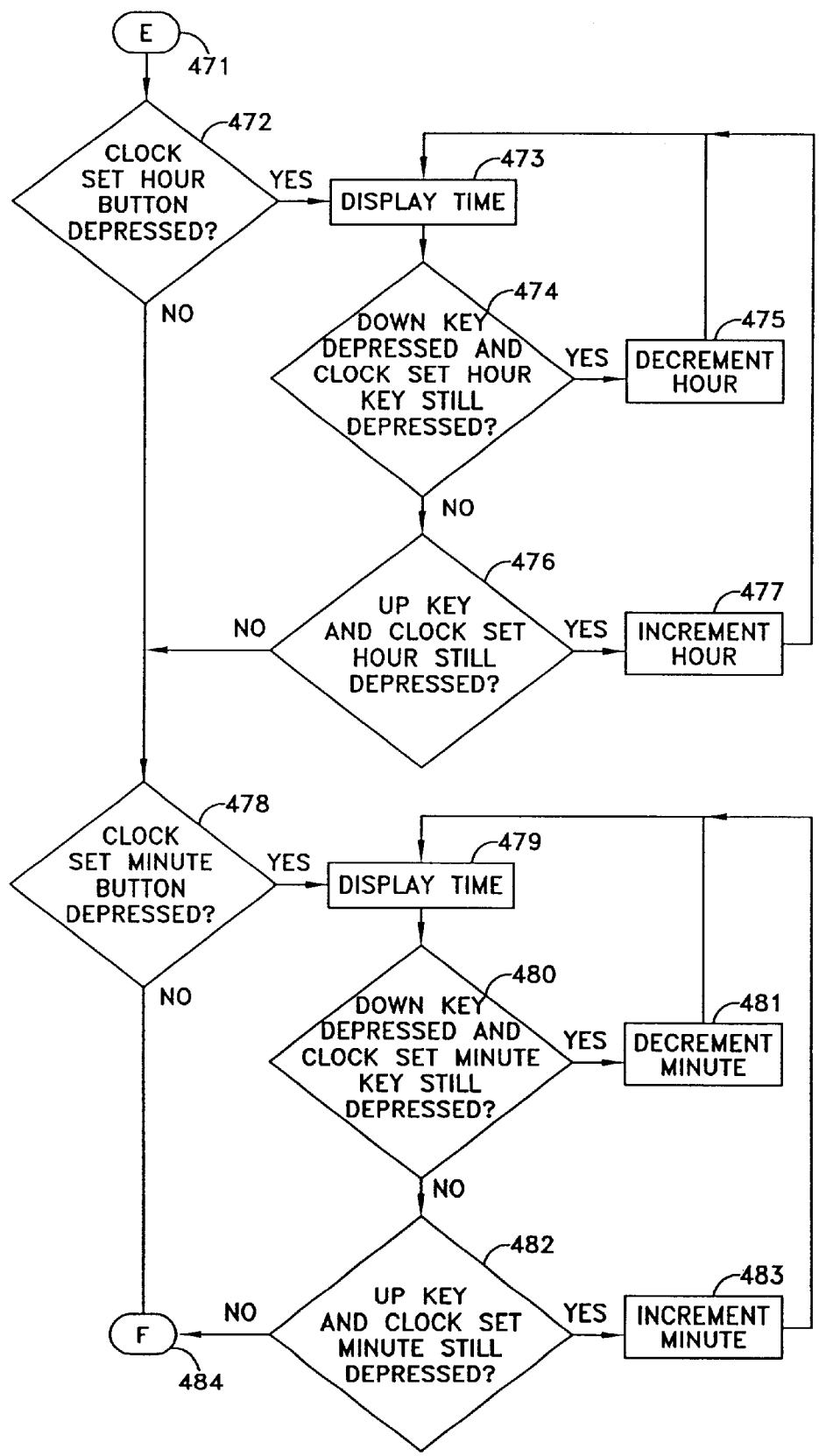
Figure 4G:
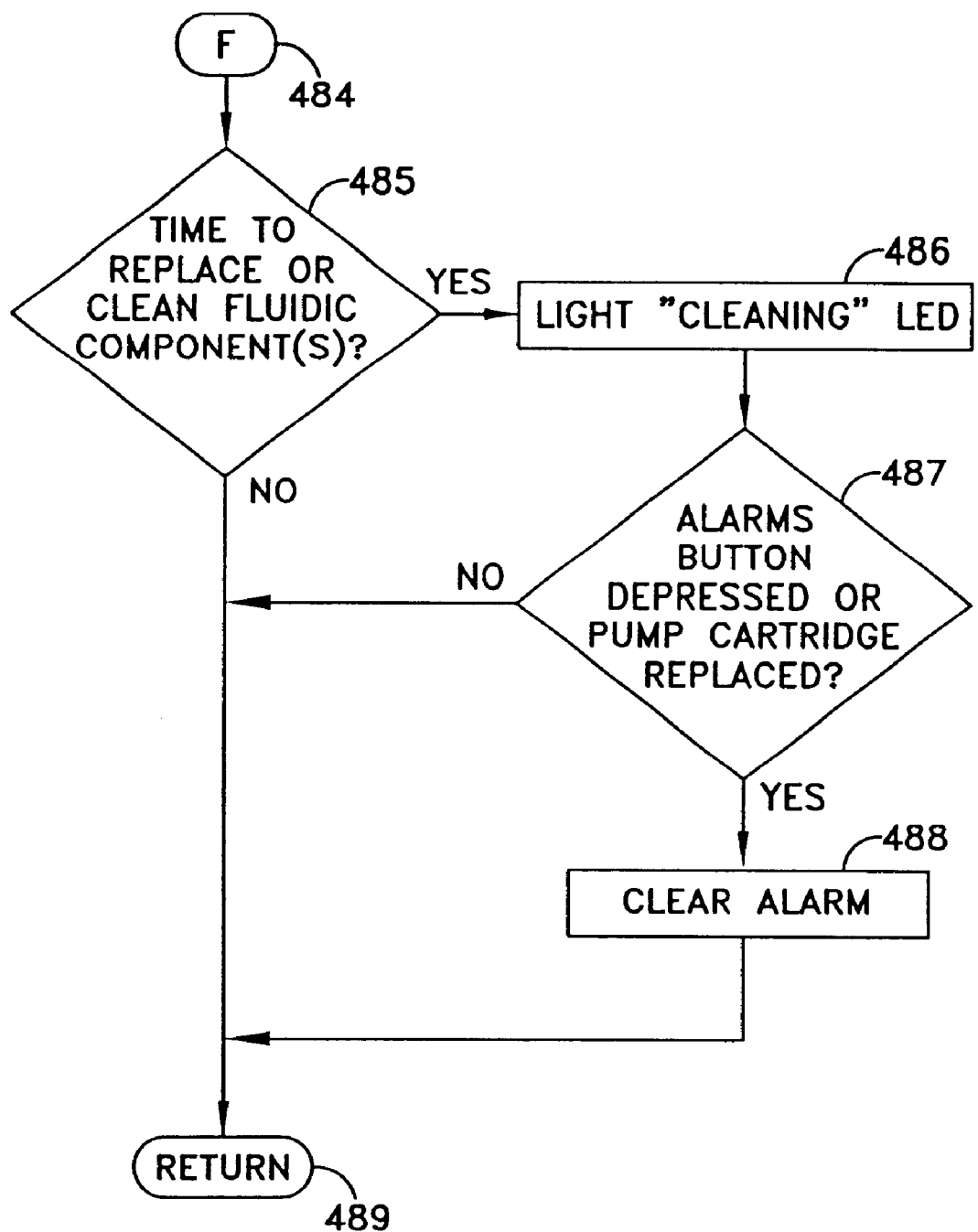

FIG. 4, which includes FIG. 4A through 4G, is a high level flow diagram of an exemplary user interface process method which may be performed by a control unit of the present invention.

Figure 5:
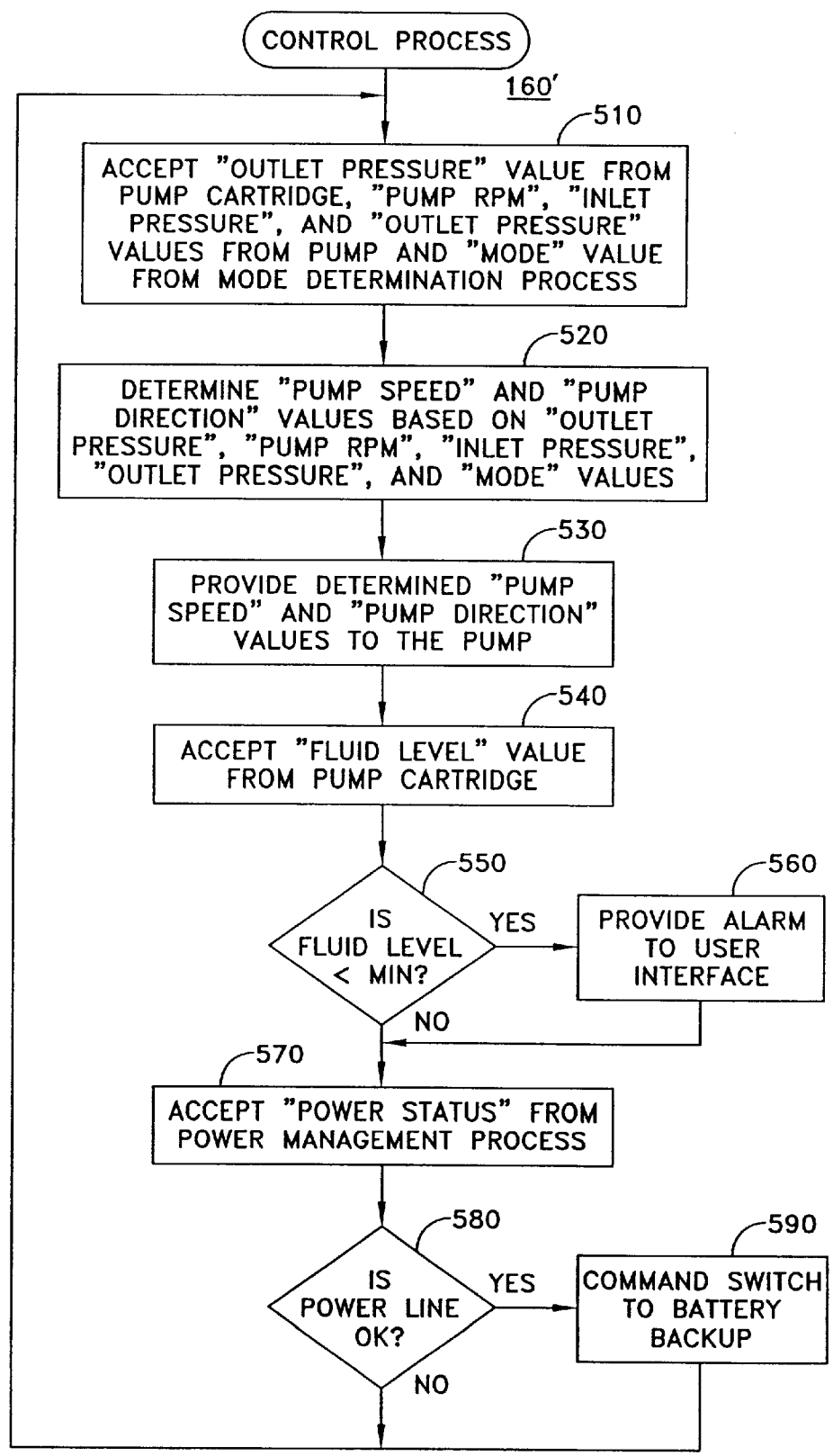

FIG. 5 is a high level flow diagram of an exemplary control process method which may be performed by a control unit of the present invention.

Figure 6:
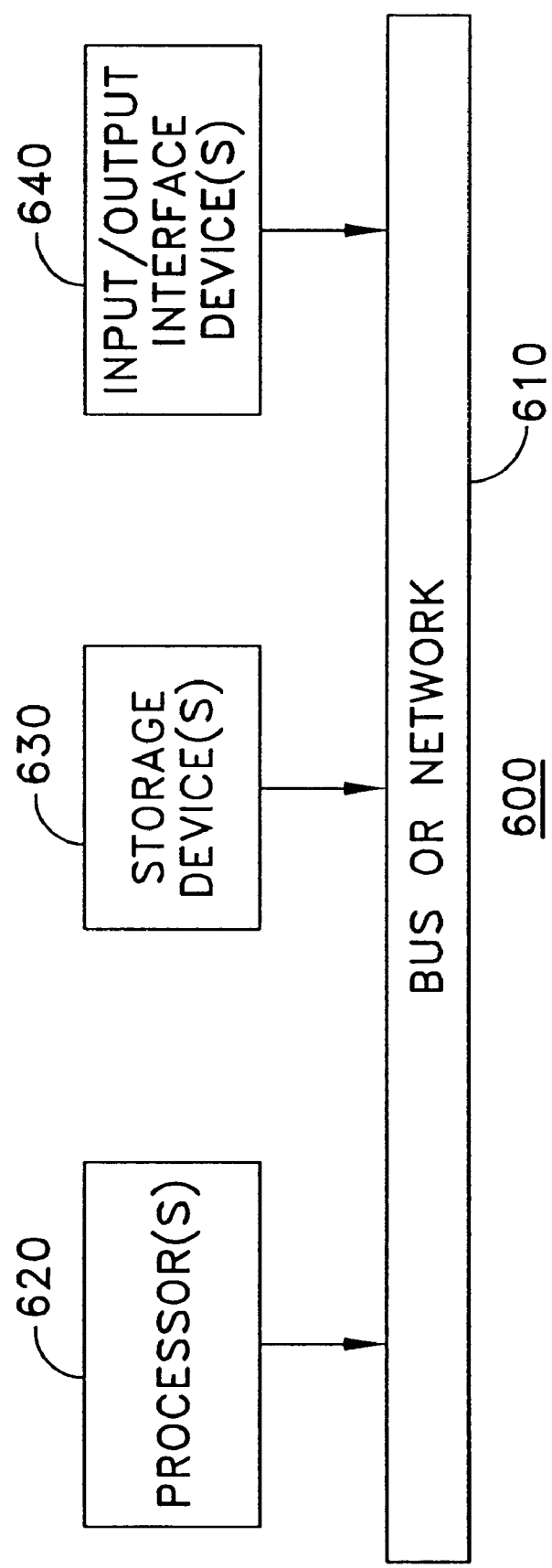

FIG. 6 is a high level block diagram of components which may be used to effect at least some of the processes which may be performed by the present invention.

Figure 7:
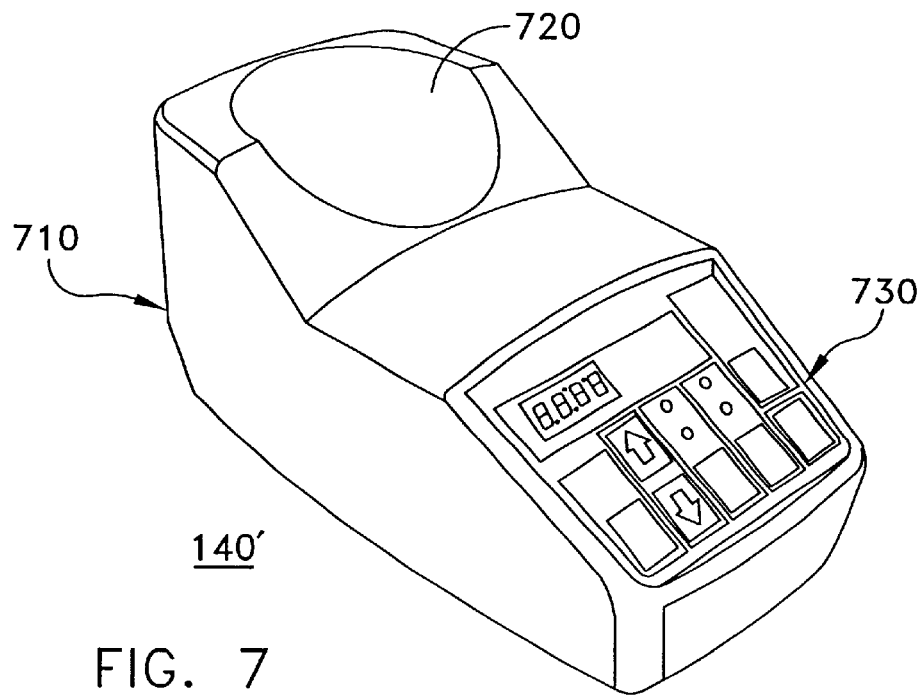

FIG. 7 is perspective view of the outer surface of a control unit which may be used by the present invention.

Figure 8:
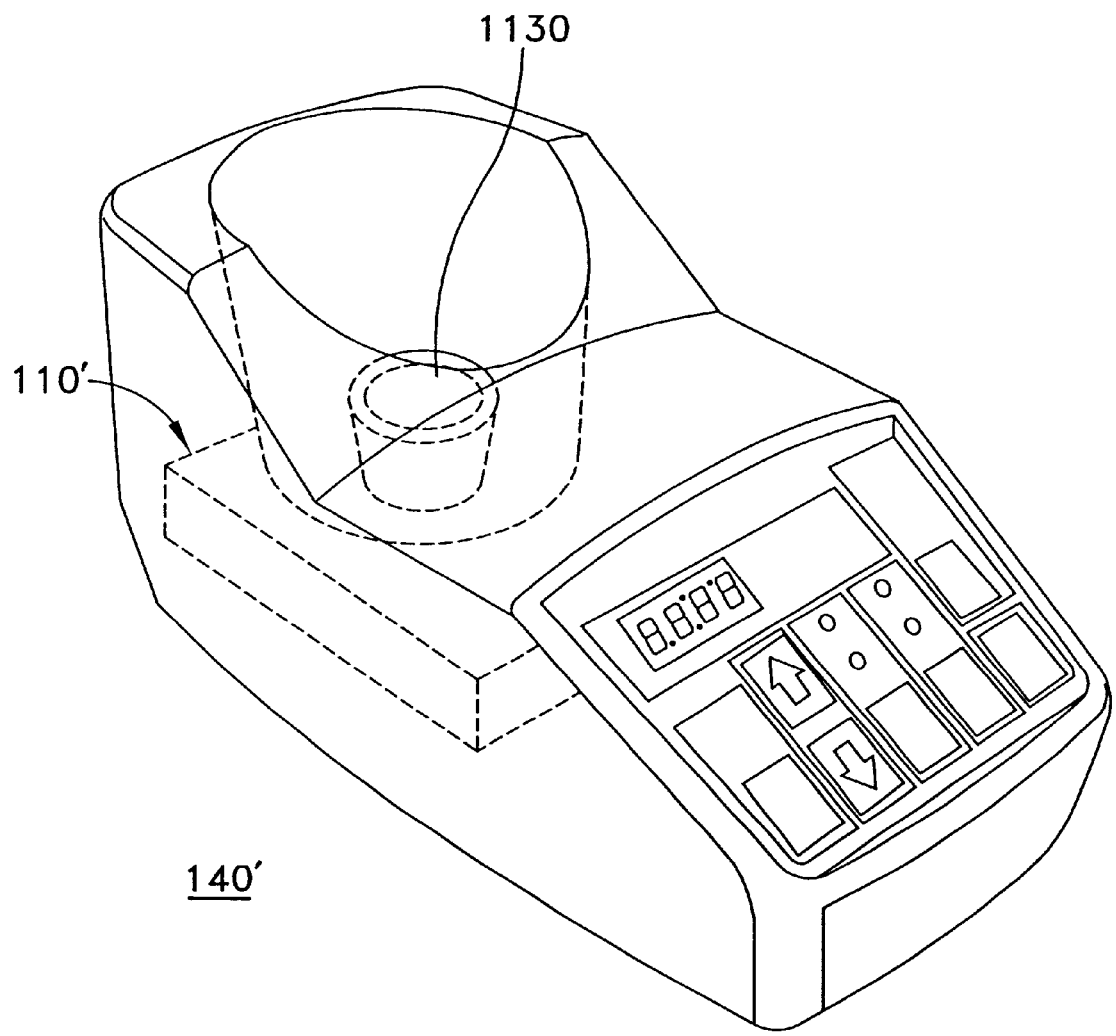

FIG. 8 is a partial transparent perspective view of the control unit of FIG. 7.

Figure 9:
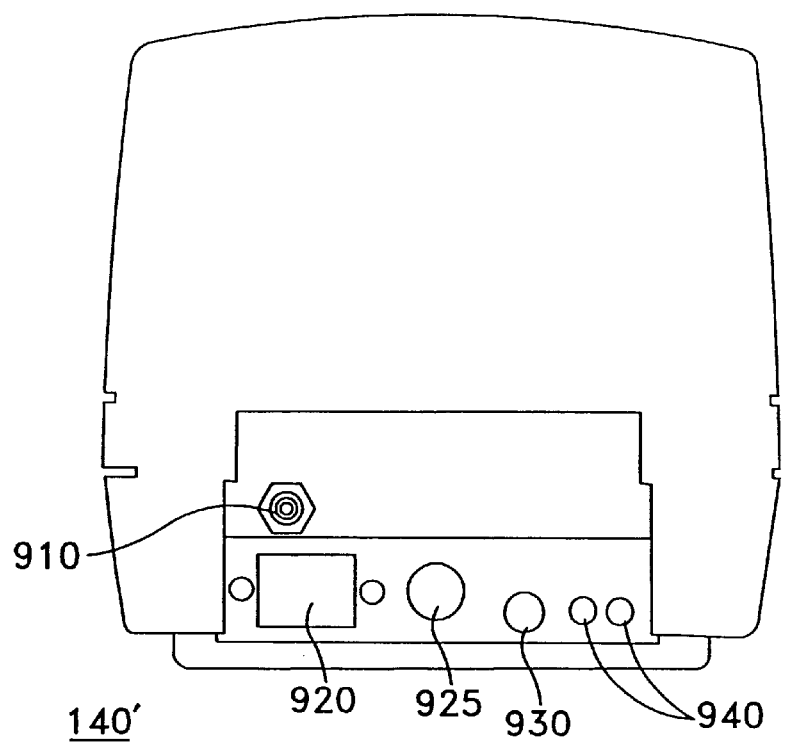

FIG. 9 is a rear view of the outer surface of the control unit.

Figure 10:
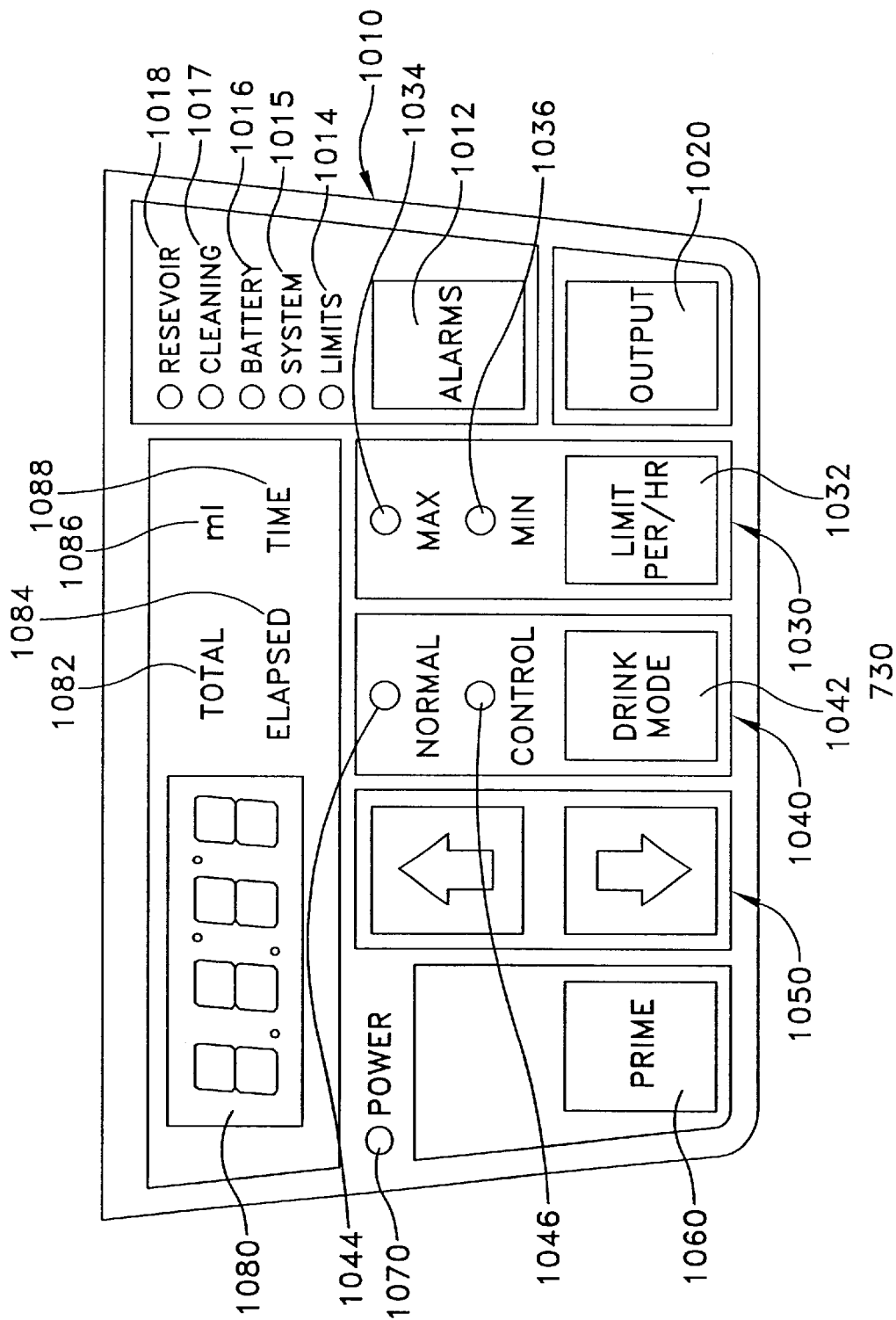

FIG. 10 illustrates a front panel which may be provided on the control unit.

Figure 11A:
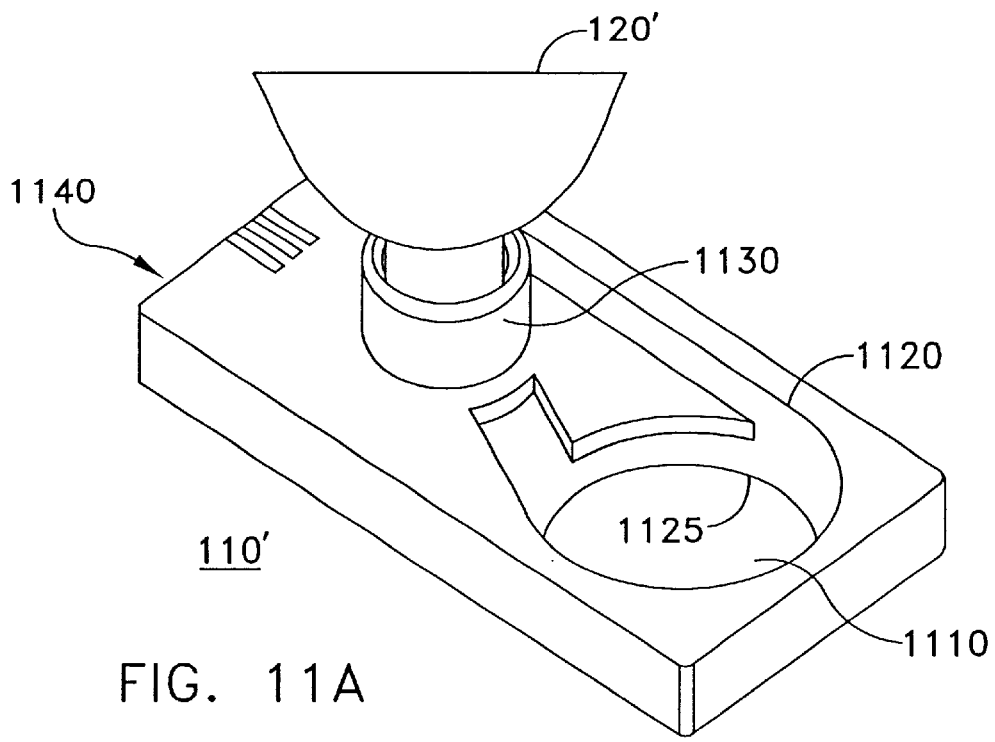

FIG. 11A is a partial transparent perspective view of a removable, disposable, pump cartridge which may be used by the present invention, in which a fluid level sensor is shown.

Figure 11B:
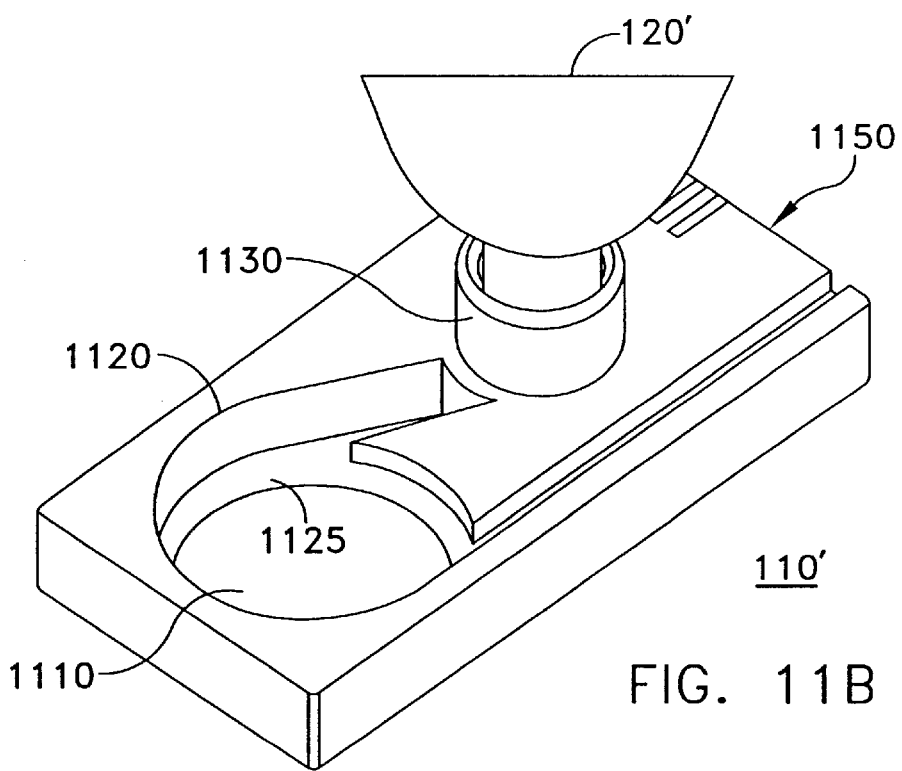

FIG. 11B is a partial transparent perspective view of the removable, disposable, pump cartridge of FIG. 11A, in which a outlet pressure sensor is shown.

Figure 12A:
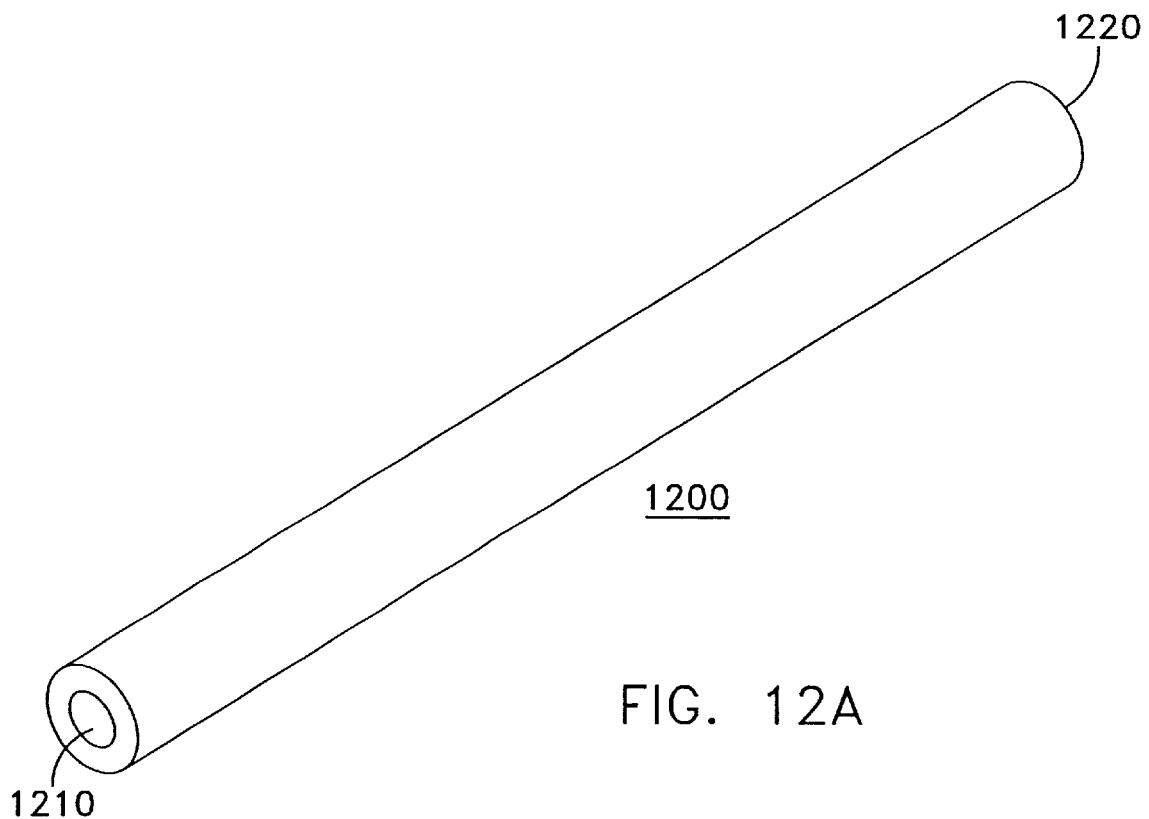
Figure 12B:
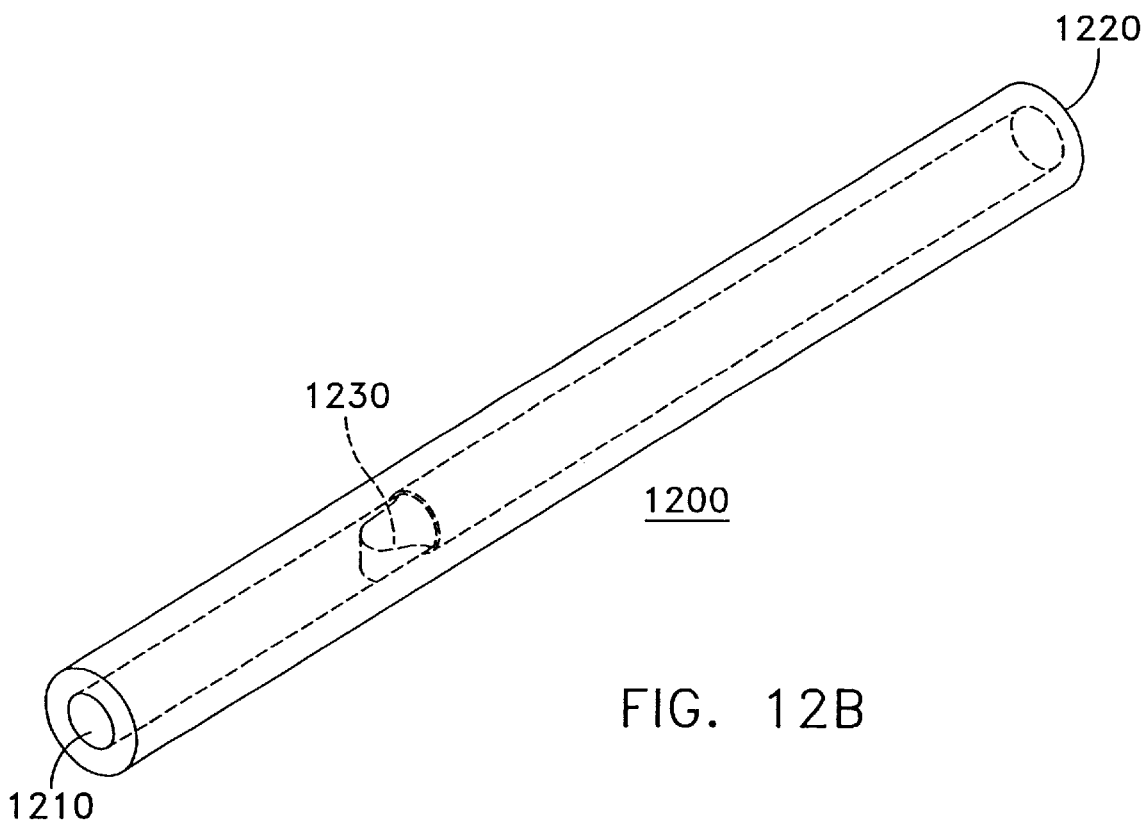

FIG. 12A is a perspective view, and FIG. 12B is a partial transparent perspective view, of a sip tip oral fluid dispenser which may be used by the present invention.

Figure 13A:
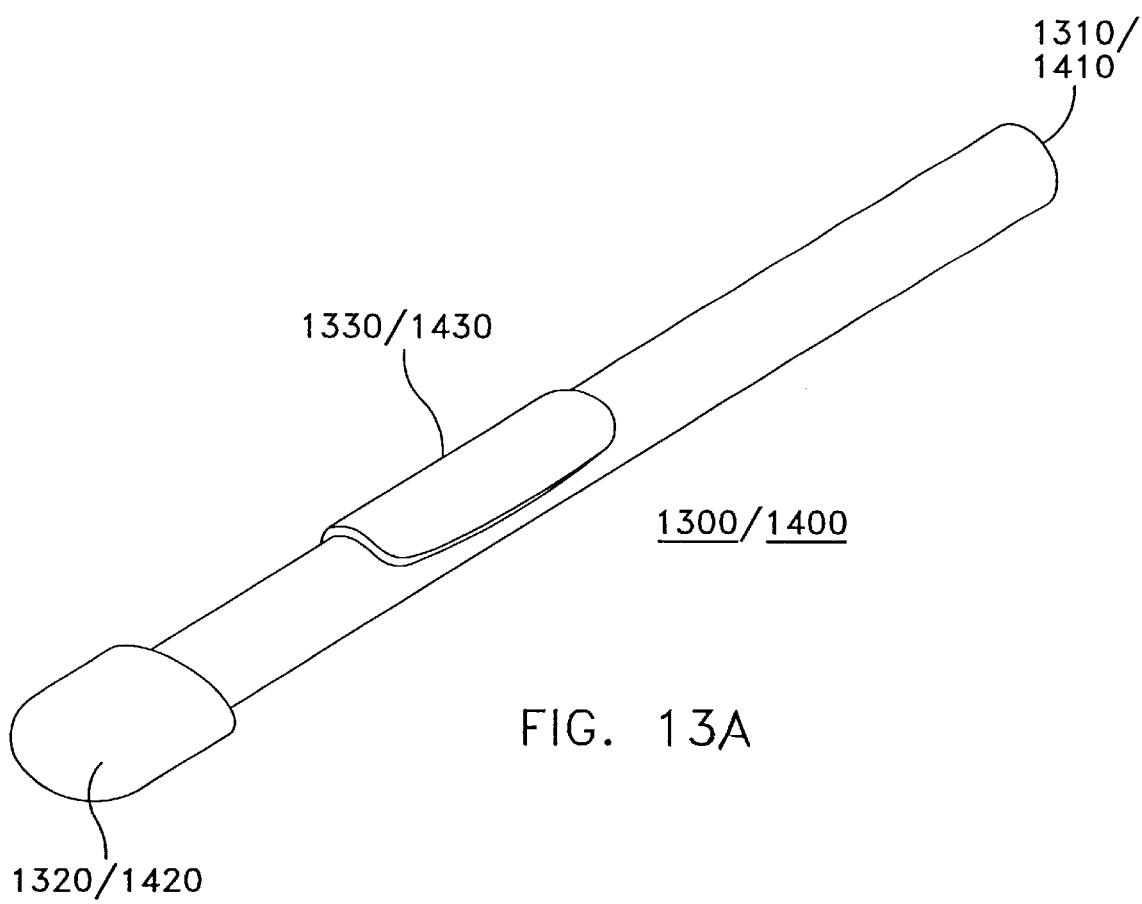
Figure 13B:
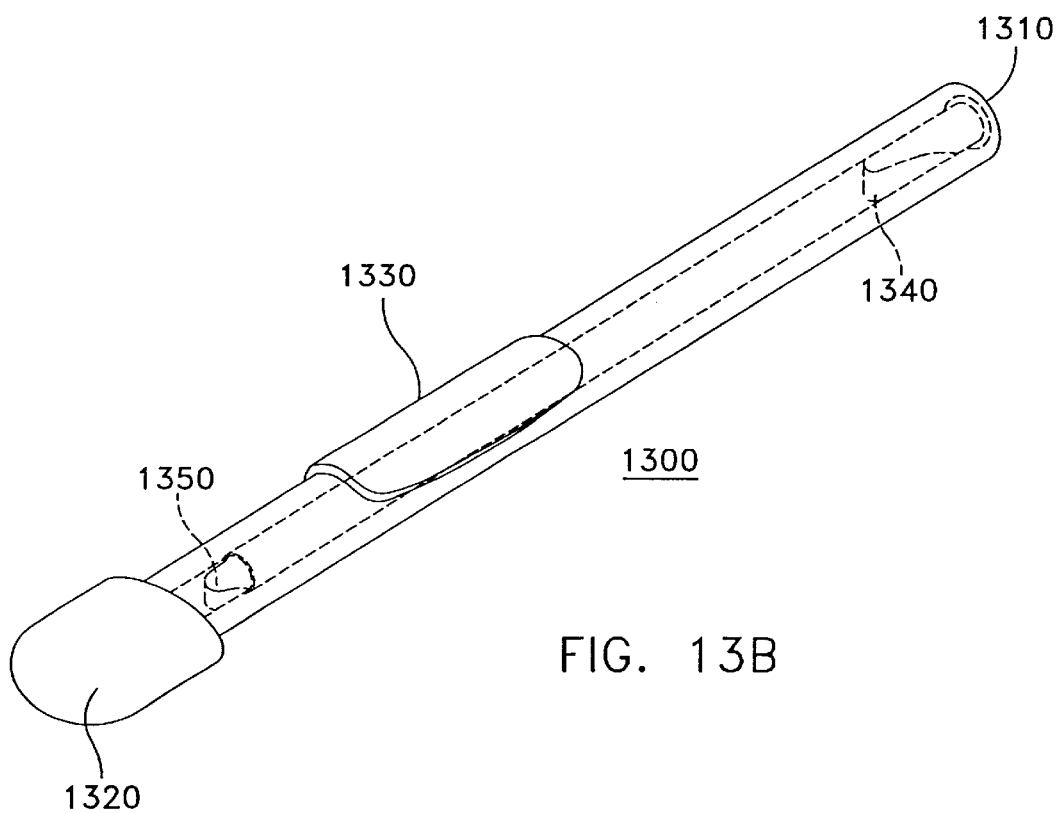

FIG. 13A is a perspective view, and FIG. 13B is a partial transparent perspective view, of a pump swab tip oral fluid dispenser which may be used by the present invention.

Figure 14A:
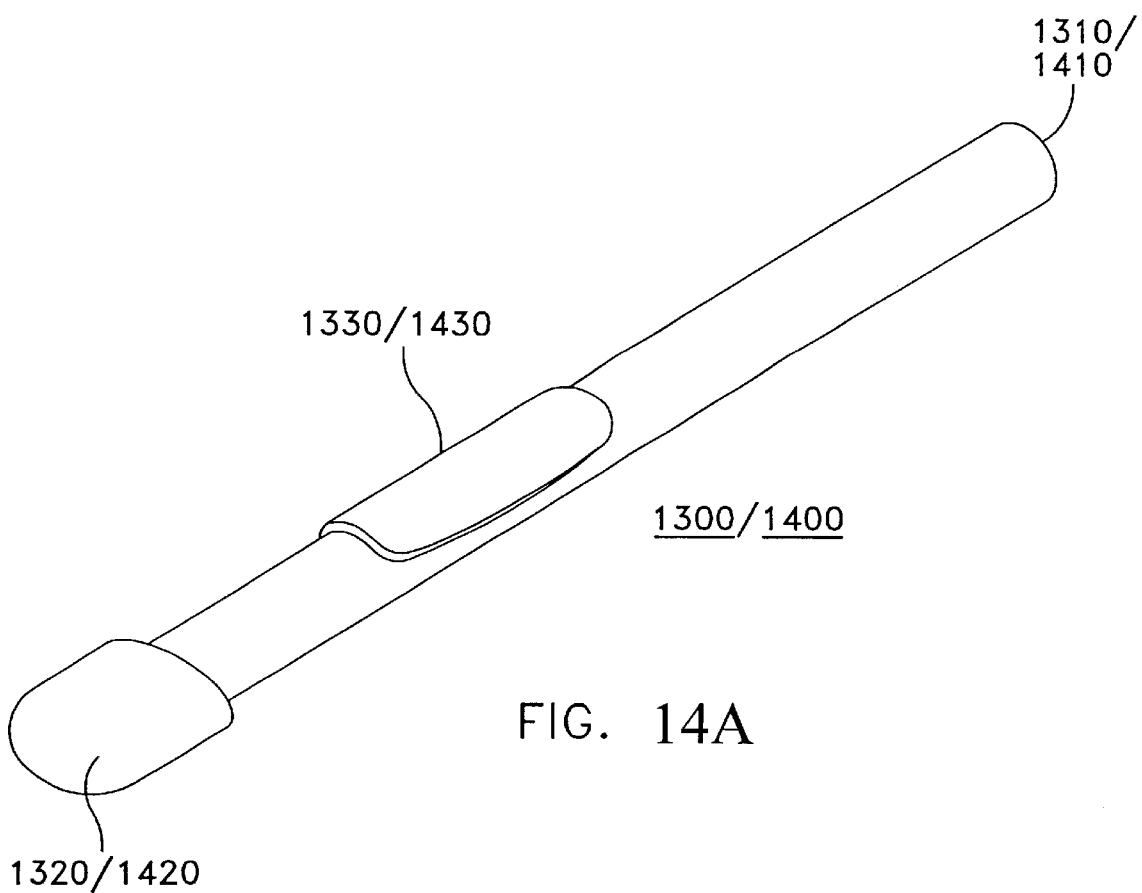
Figure 14B:
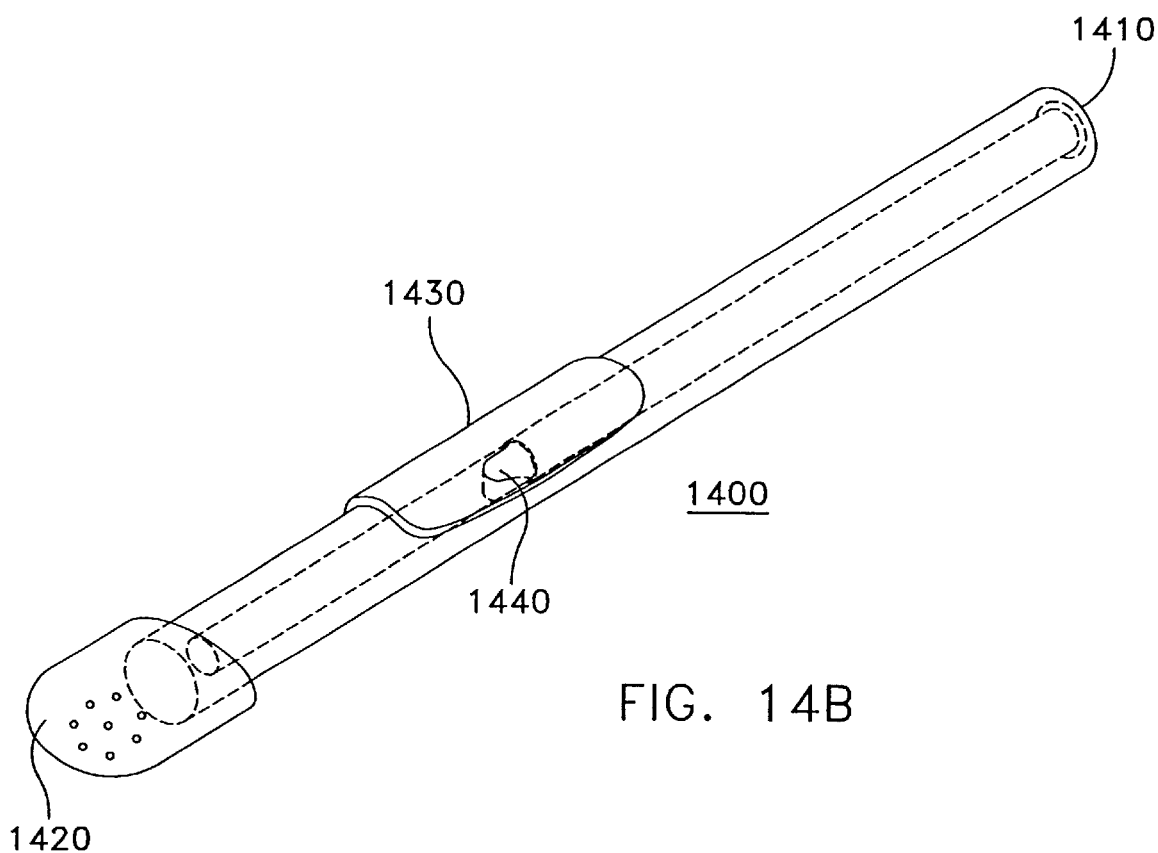

FIG. 14A is a perspective view, and FIG. 14B is a partial transparent perspective view, of a swab tip oral fluid dispenser which may be used by the present invention.

Figure 15A:
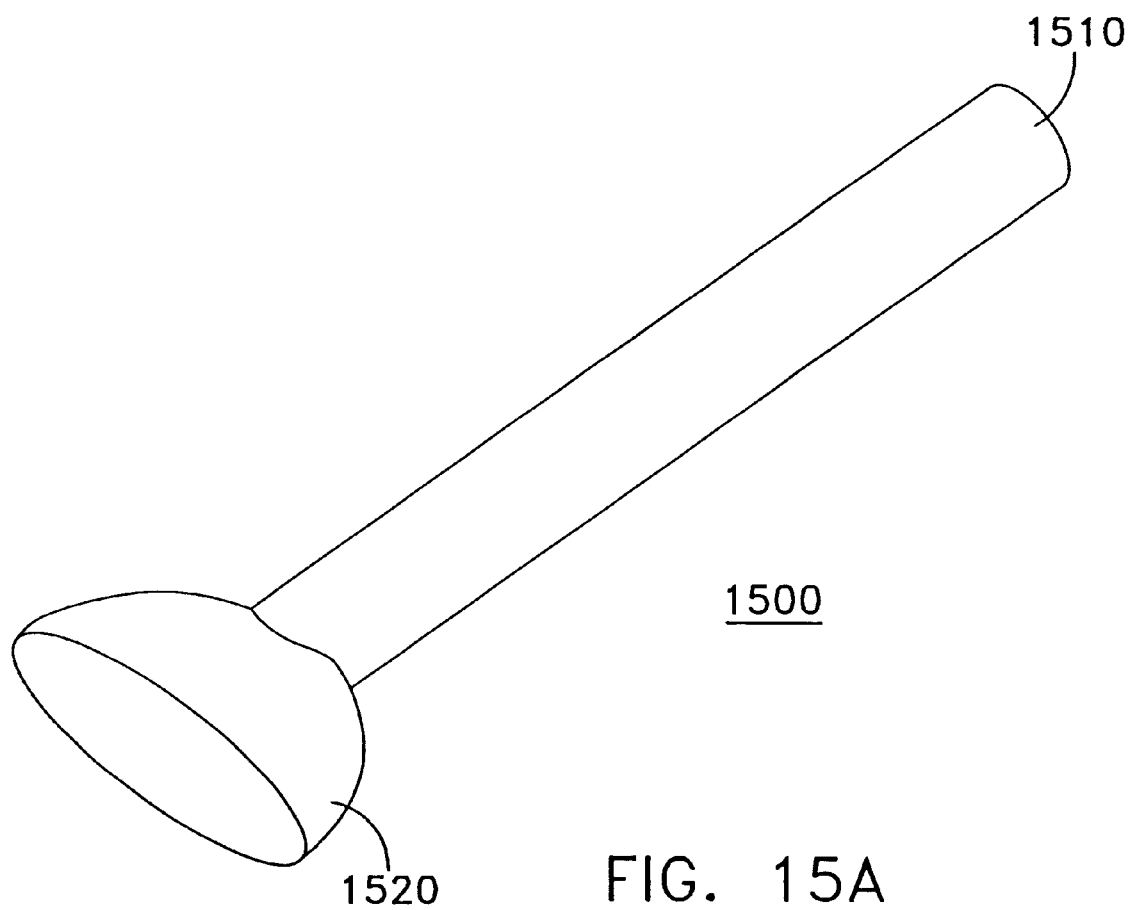
Figure 15B:
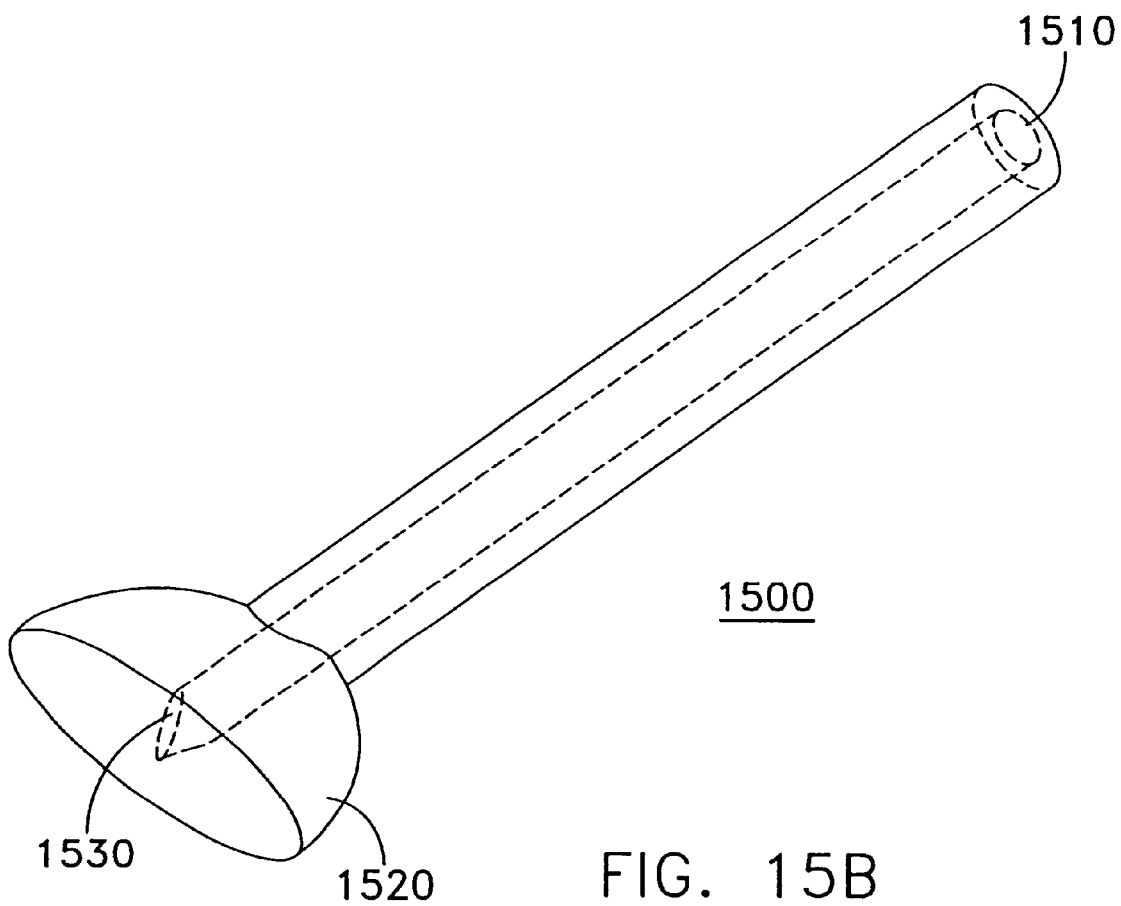

FIG. 15A is a perspective view, and FIG. 15B is a partial transparent perspective view, of a bite valve oral fluid dispenser which may be used by the present invention.

Figure 16A:
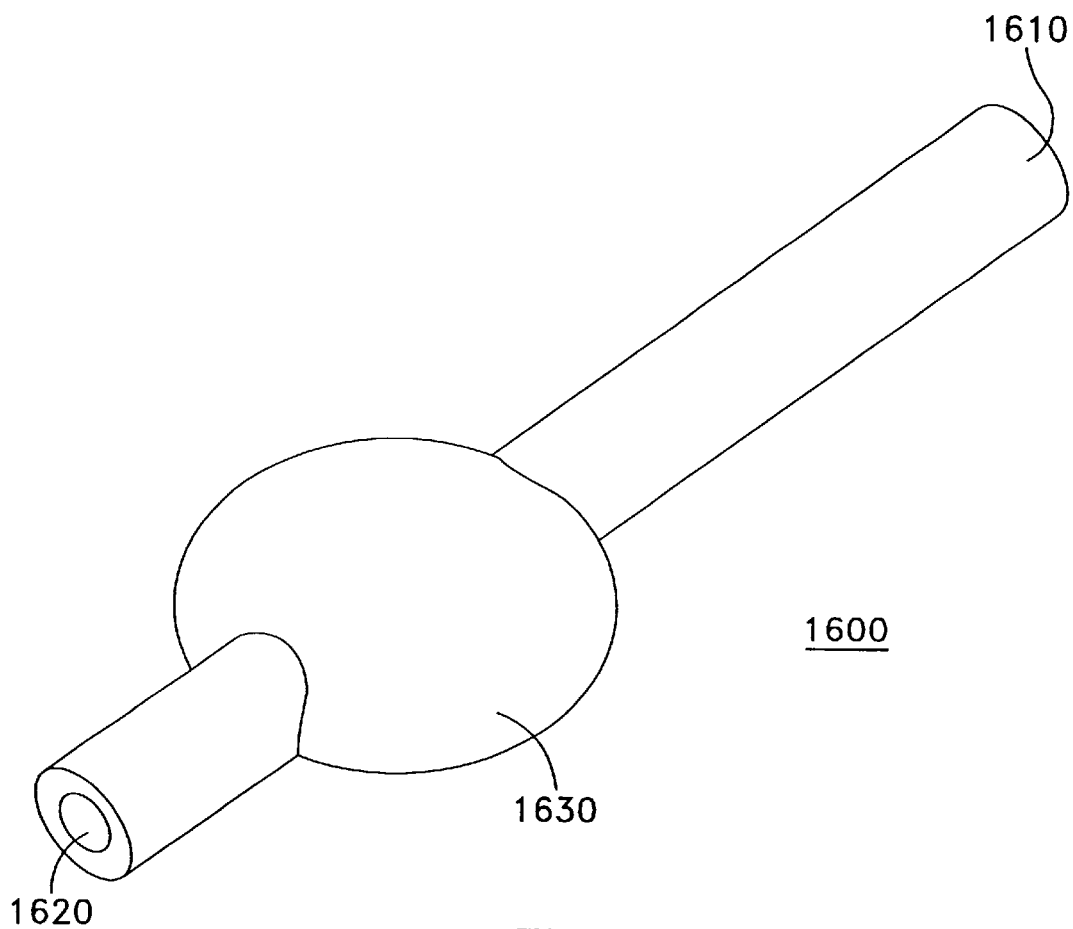
Figure 16B:
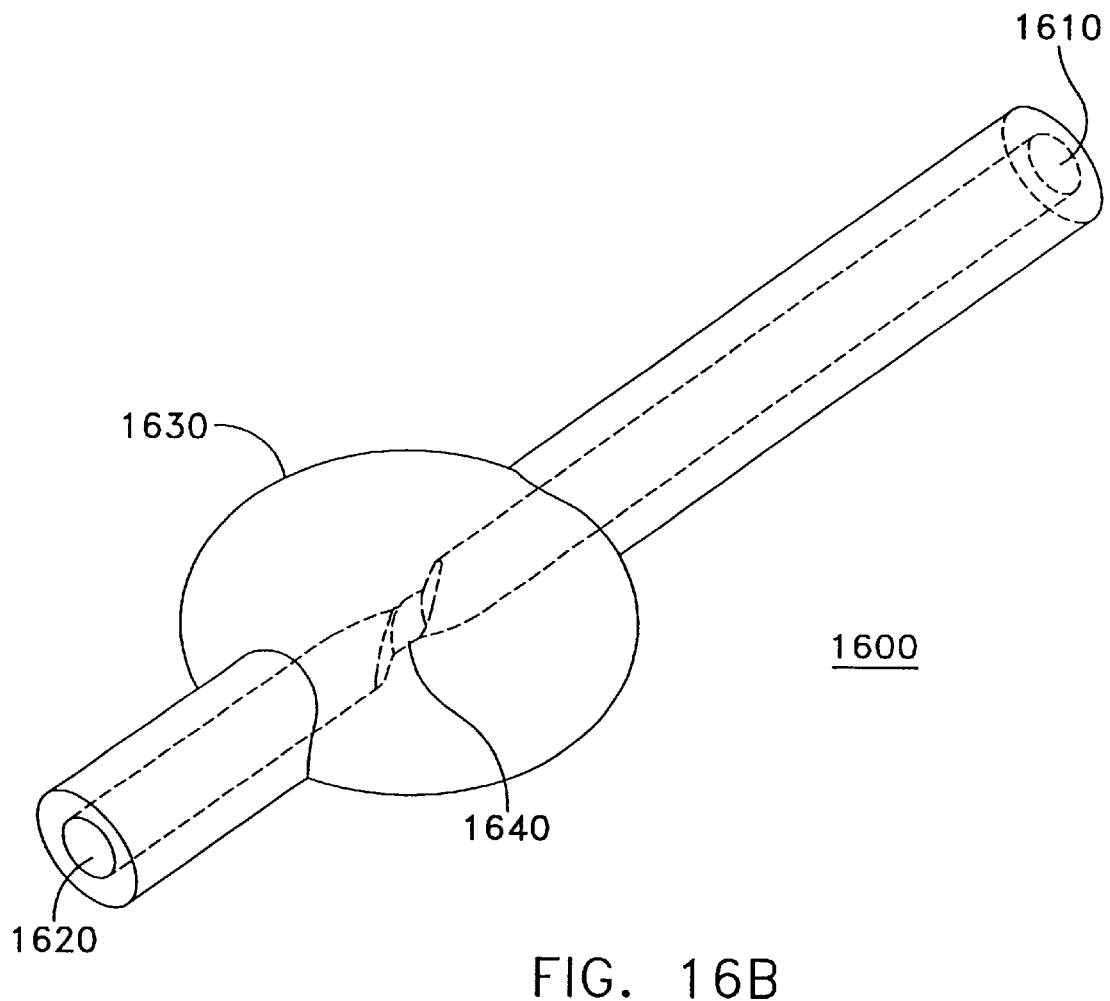

FIG. 16A is a perspective view, and FIG. 16B is a partial transparent perspective view, of a drink straw oral fluid dispenser which may be used by the present invention.

Figure 17A:
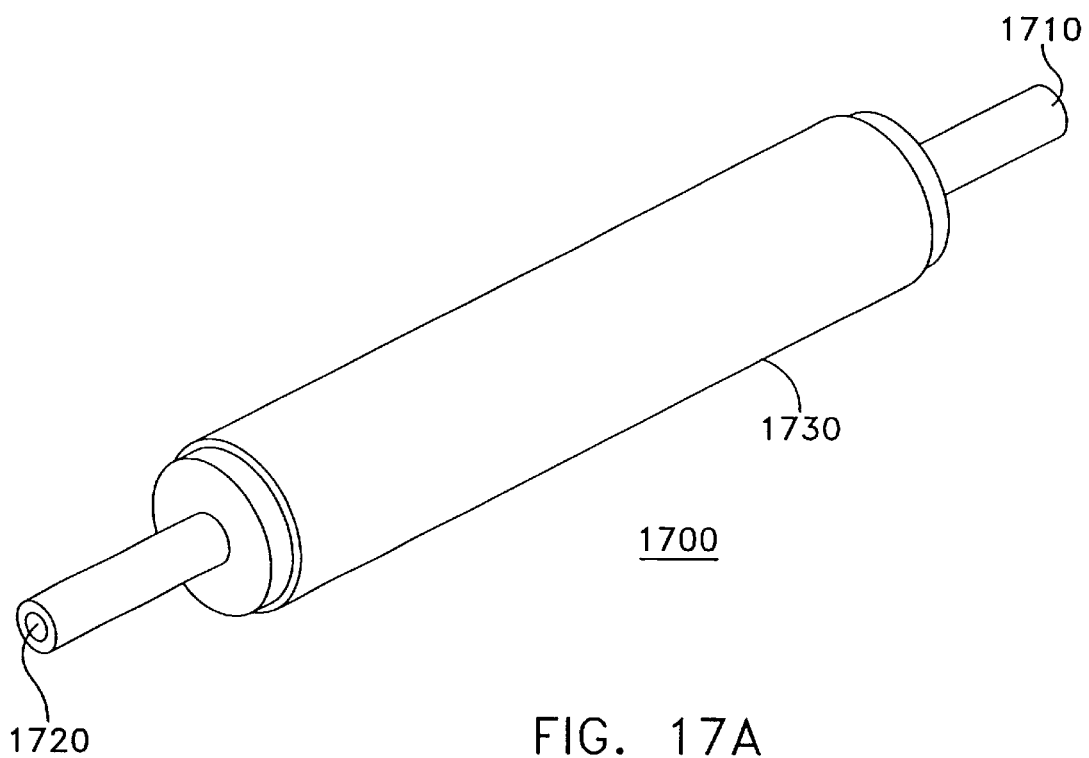
Figure 17B:
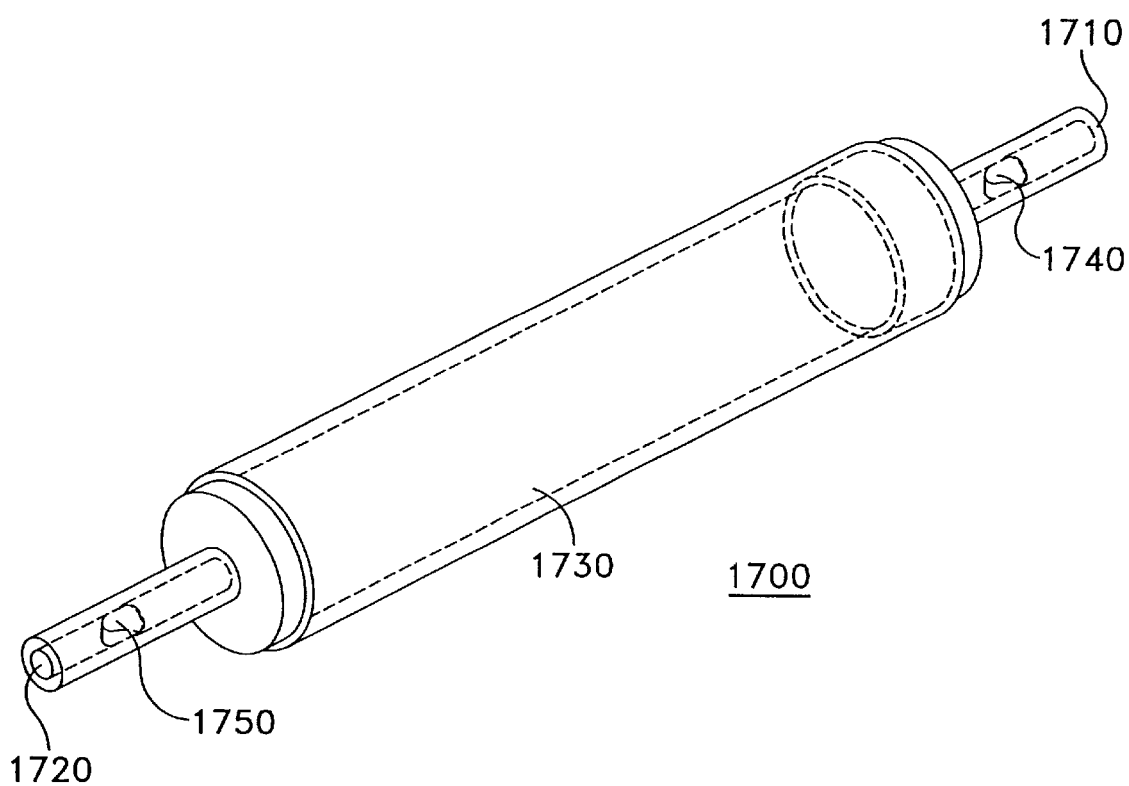

FIG. 17A is a perspective view, and FIG. 17B is a partial transparent perspective view, of a squeezer oral fluid dispenser which may be used by the present invention.

Figure 18A:
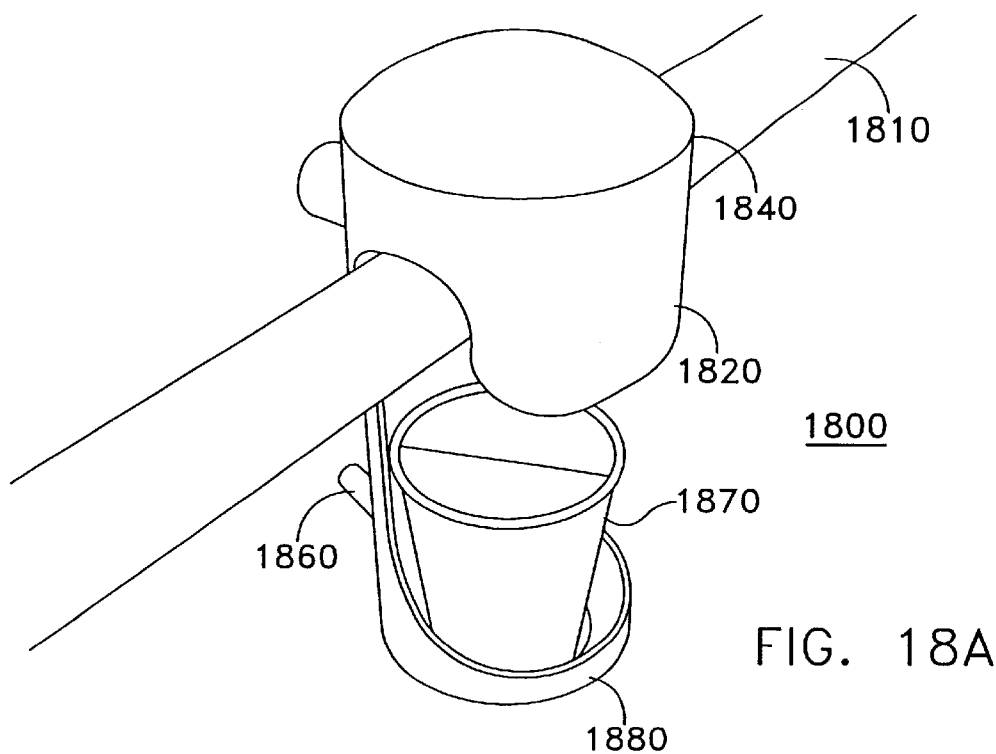
Figure 18B:
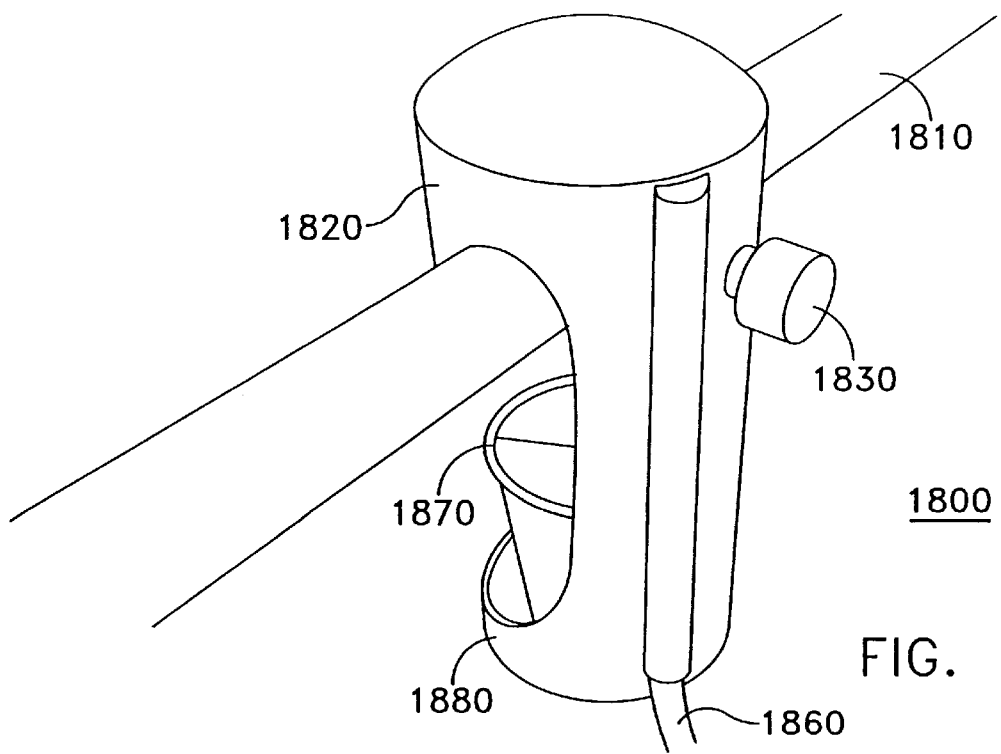

FIG. 18A is front perspective view, and FIG. 18B is a rear perspective view, of a bedside cup attachment oral fluid dispenser which may be used by the present invention.

Figure 19:
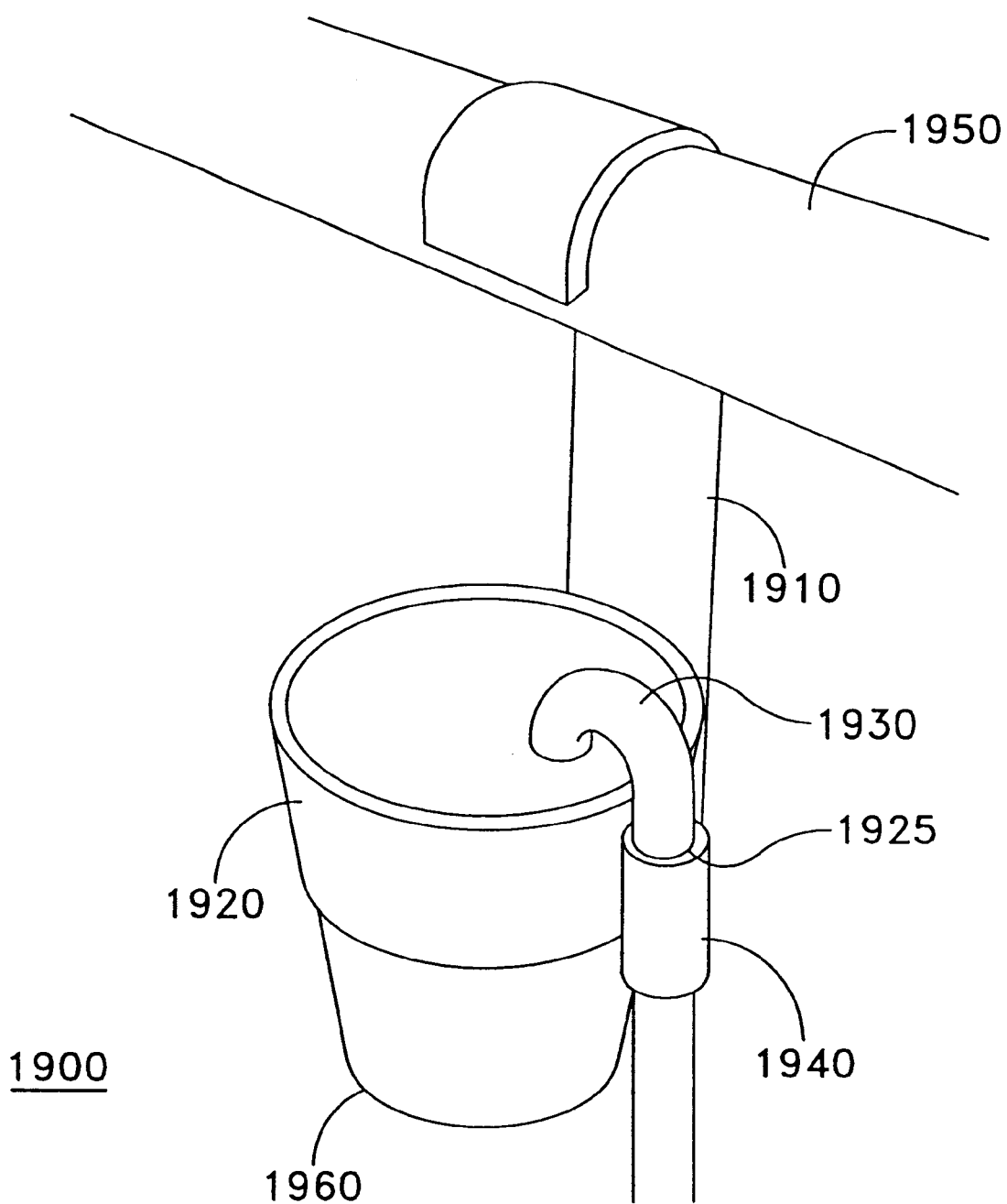

FIG. 19 is a perspective view of a tube cup oral fluid dispenser which may be used by the present invention.

Figure 20:
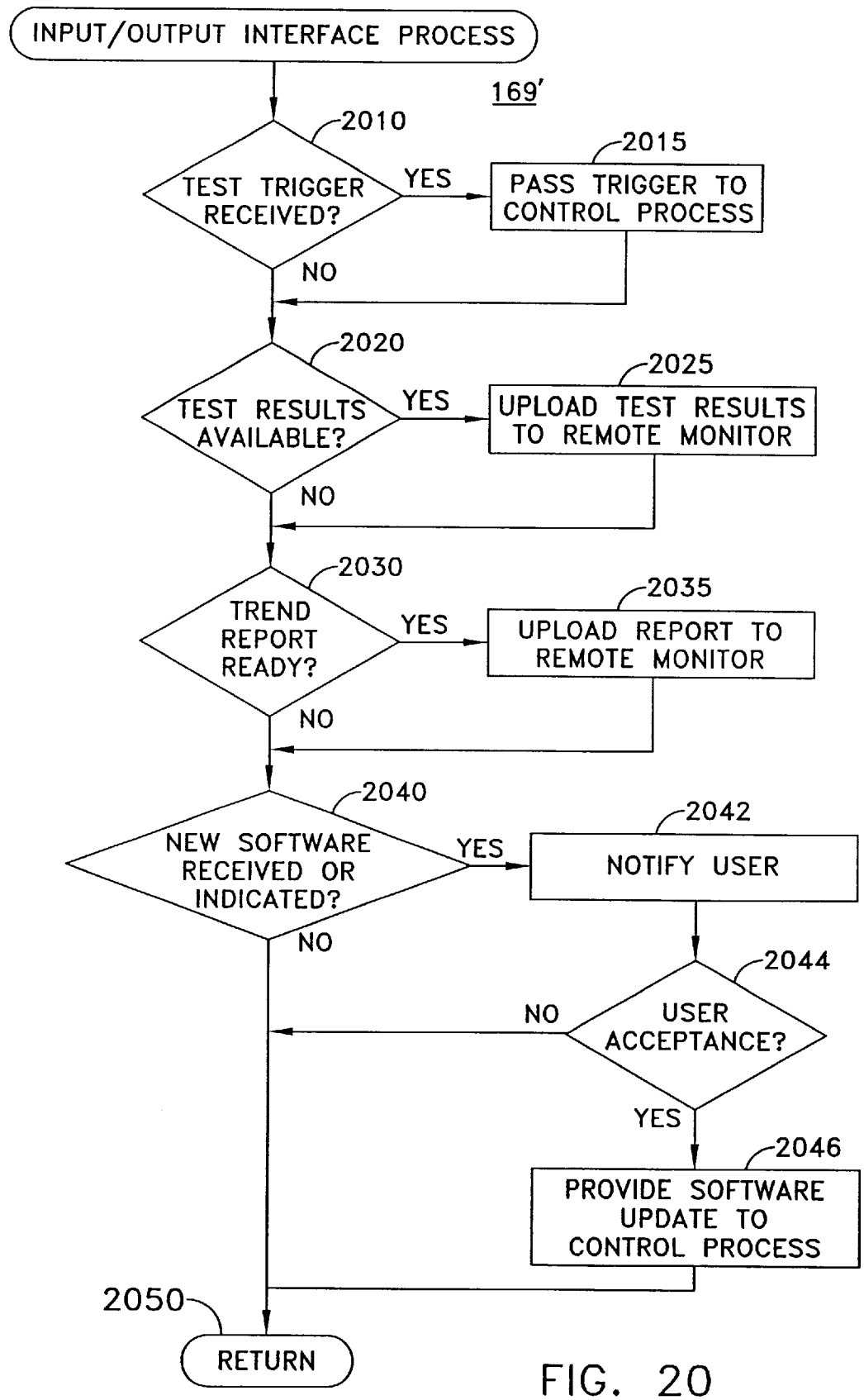

FIG. 20 is a high level flow diagram of an exemplary input/output interface process method which may be performed by a control unit of the present invention.

Figure 21A:
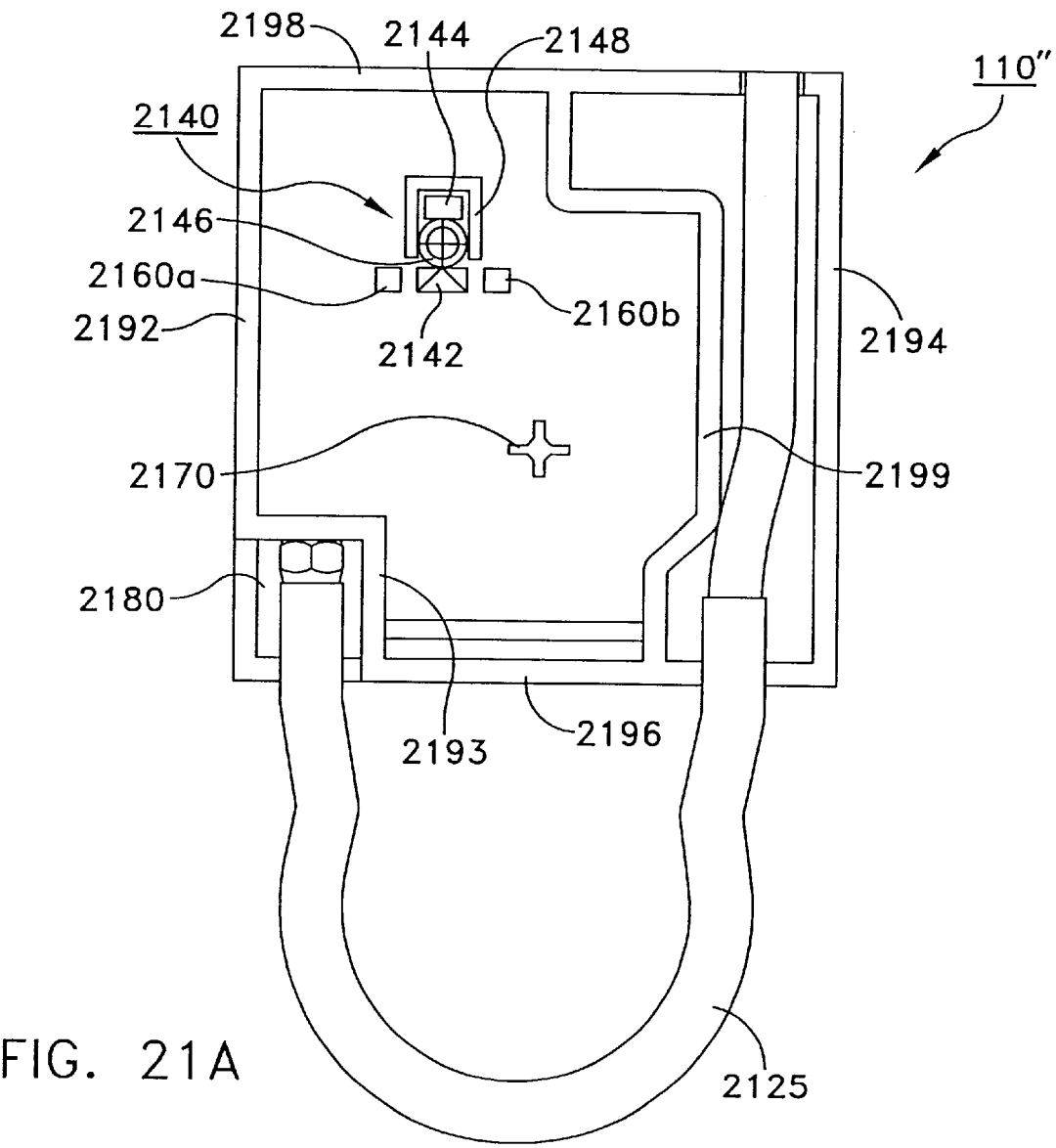
Figure 21B:
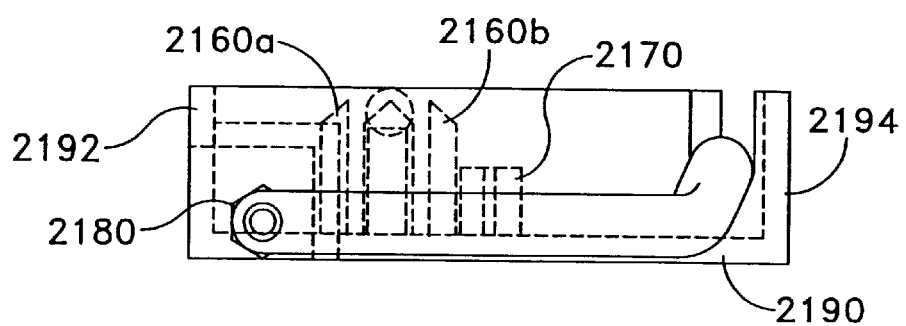
Figure 21C:
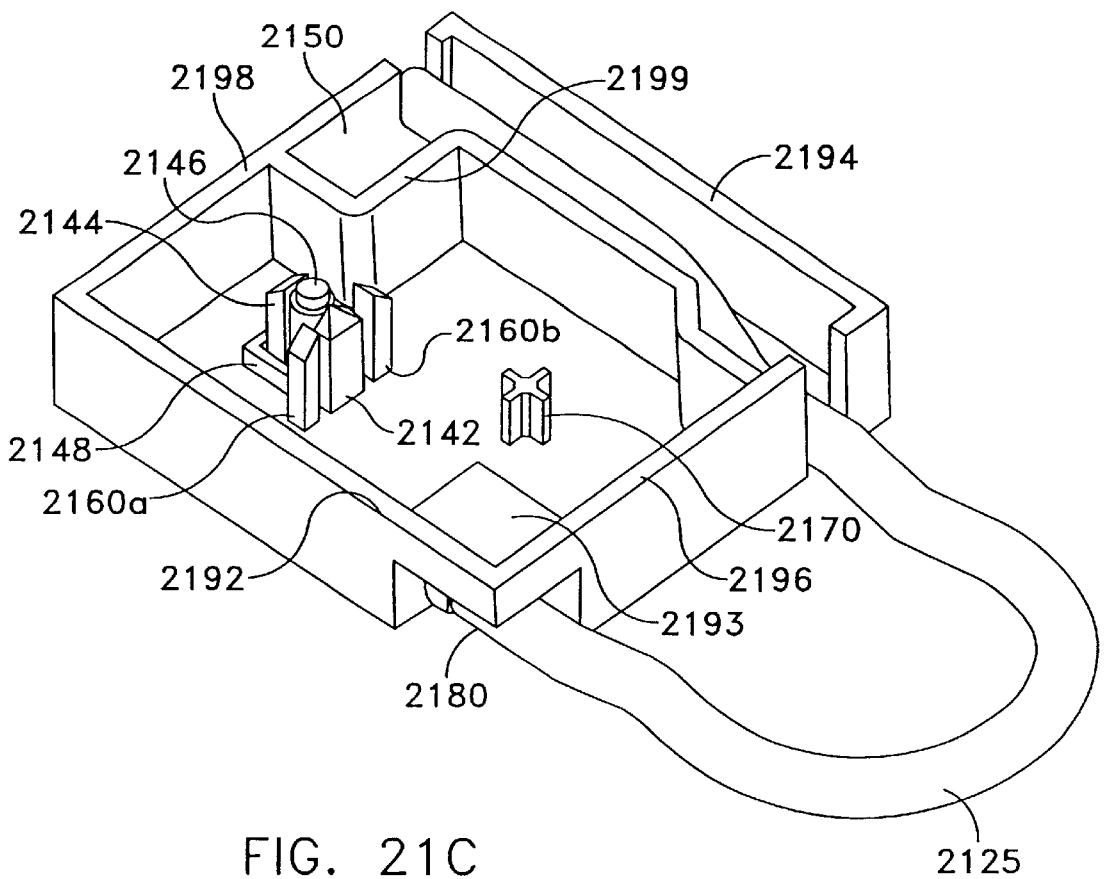
Figure 21D:
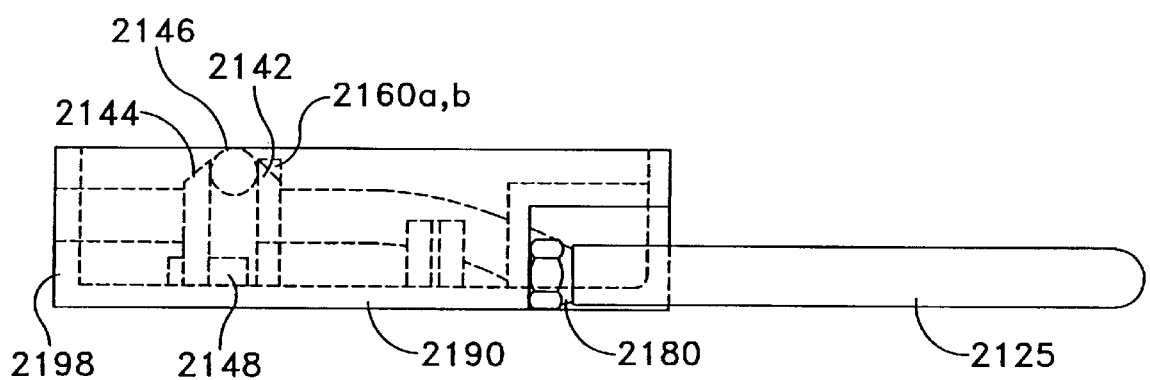
Figure 21E:
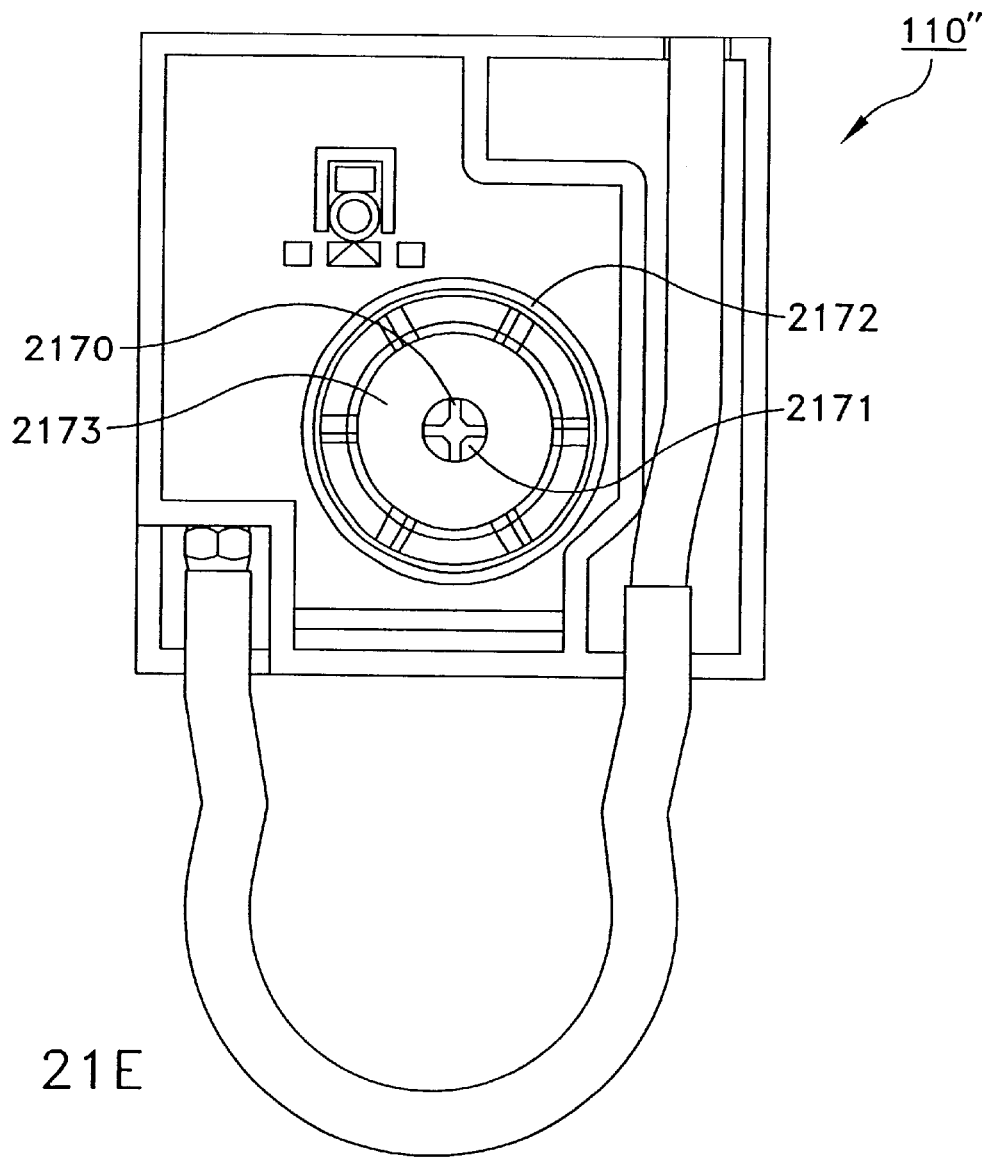
Figure 21F:
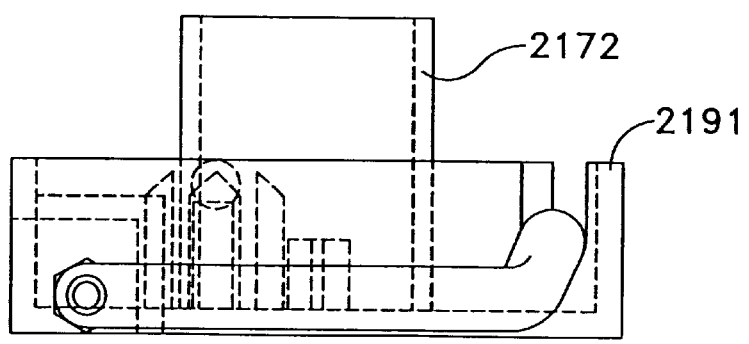
Figure 21G:
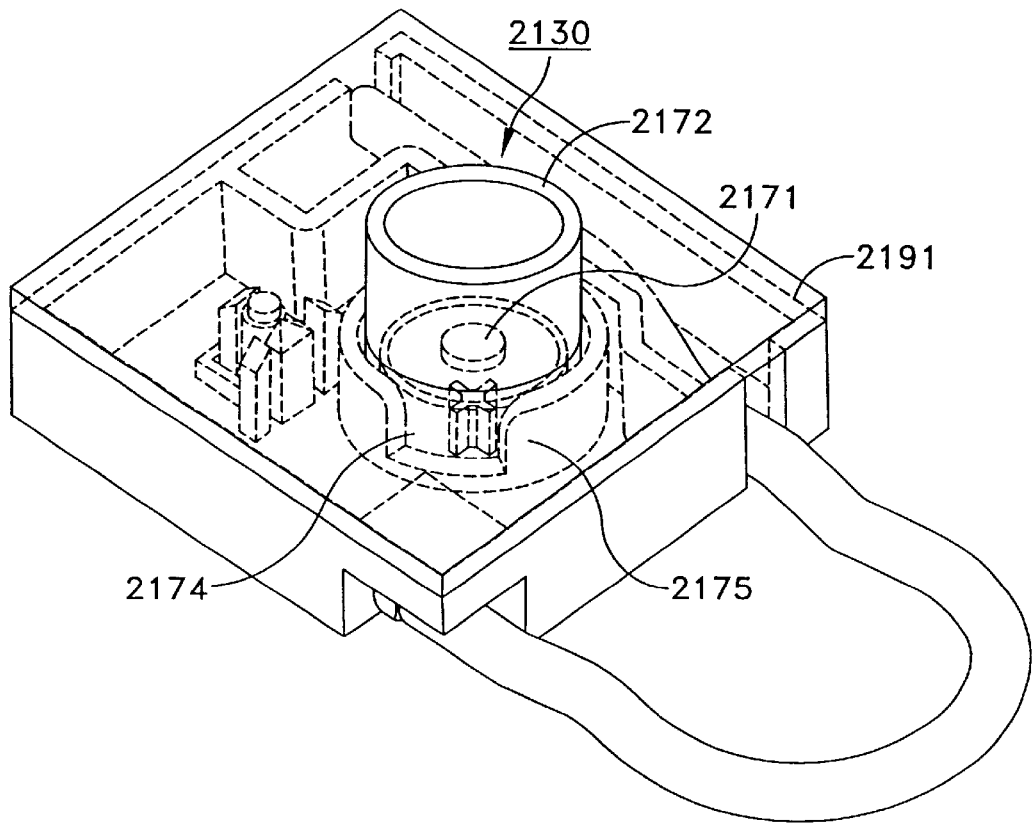
Figure 21H:
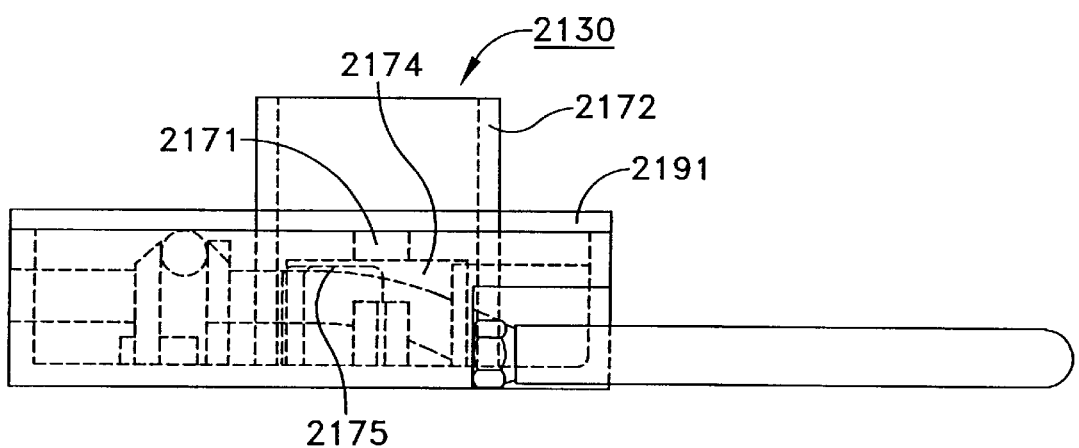

FIG. 21A is a plan view, FIG. 21B is an end view, FIG. 21C is a perspective view, and FIG. 21D is a side view of an alternative pump cartridge. FIG. 21E is a plan view, FIG. 21F is an end view, FIG. 21G is a perspective view, and FIG. 21H is a side view of the alternative cartridge including a fitting and a lid.

Figure 22:
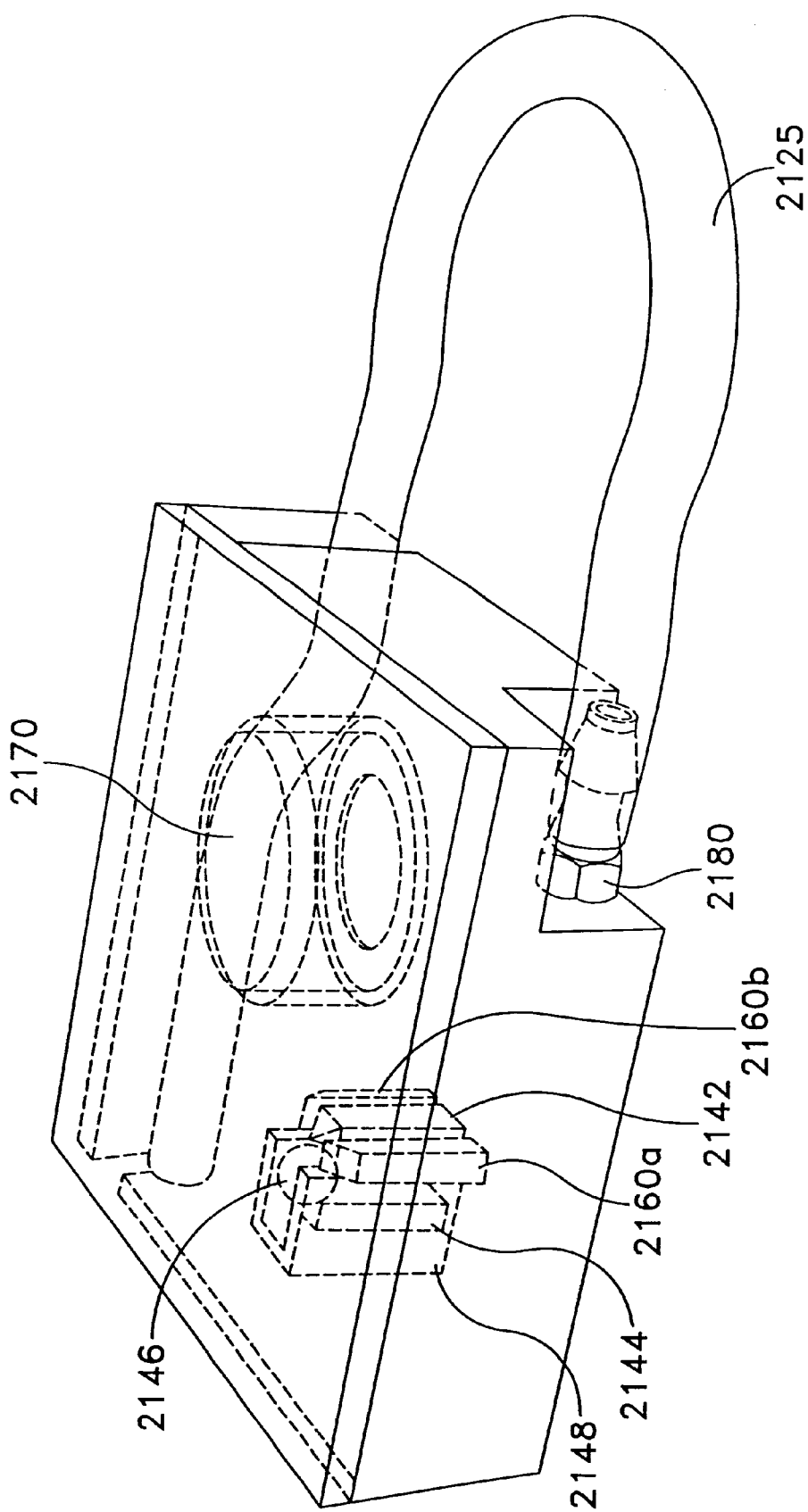

FIG. 22 is a partial transparent perspective view of the alternative pump cartridge of FIGS. 21A through 21D.

Figure 23:
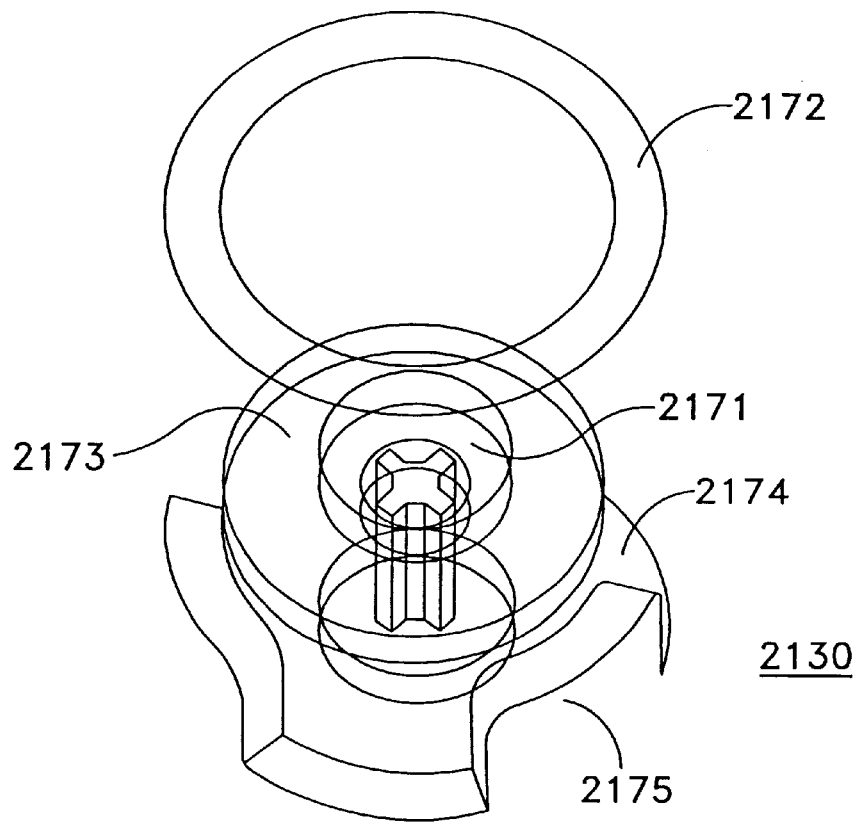

FIG. 23 is a perspective view of the fitting of FIGS. 21E through 21H.

Figures 24A, 24B:
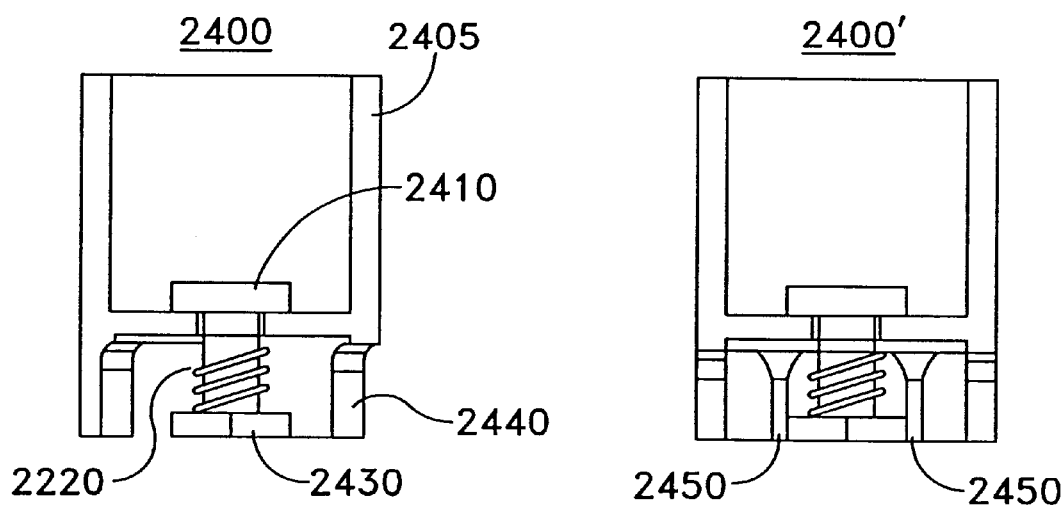

FIGS. 24A and 24B are cross-sectional side views of reservoir adapter caps which may be used with the pump cartridges of the present invention.

§4. DETAILED DESCRIPTION

The present invention concerns novel methods and apparatus for delivering fluids orally. The following description is presented to enable one skilled in the art to make and use the invention, and is provided in the context of particular applications and their requirements. Various modifications to the disclosed embodiments will be apparent to those skilled in the art, and the general principles set forth below may be applied to other embodiments and applications. Thus, the present invention is not intended to be limited to the embodiments shown.

In the following, basic functions which may be performed by the present invention will first be described in §4.1. Then, exemplary embodiments and exemplary methods of the present invention will be described in §4.2. Finally, examples of the operation of the present invention will be described in §4.3.

§4.1 Functions which May be Performed

A first main function of the present invention is to deliver fluids. The present invention does so by providing a pump (such as a peristaltic pump, for example), a pump cartridge, a fluid reservoir, and a variety of fluid dispensers, including oral fluid dispensers. Since a number of oral fluid dispensers is provided, the one best suited for the needs of a particular application can be selected. The operation of the pump may be controlled, at least in part, based on the type of fluid dispenser being used. Further, a selectable mode can be used to further control the operation of the pump.

A second main function which may be performed by the present invention is to monitor the amount of fluids delivered over given periods of time. If too much or too little fluid is delivered (and presumably consumed), the present invention may provide a reminder (such as an audio and/or visual alarm, for example). The thresholds for such alarm conditions may be set and modified by a user.

Another function which may be performed by the present invention is to monitor the state of the fluid delivery system itself. Yet another function which may be performed by the present invention is monitoring trends in fluid delivery. Other functions which may be performed by the present invention will become apparent to those skilled in the art from the following description.

§4.2 Exemplary Embodiment(s)

In the following, the present invention will be described, at a high level, in §4.2.1. Various subassemblies and components of the present invention will then be described in §4.2.2. Finally, exemplary methods for performing processes discussed in §4.2.1 are described in §4.2.3.

§4.2.1 Process Diagram

Figure 1:
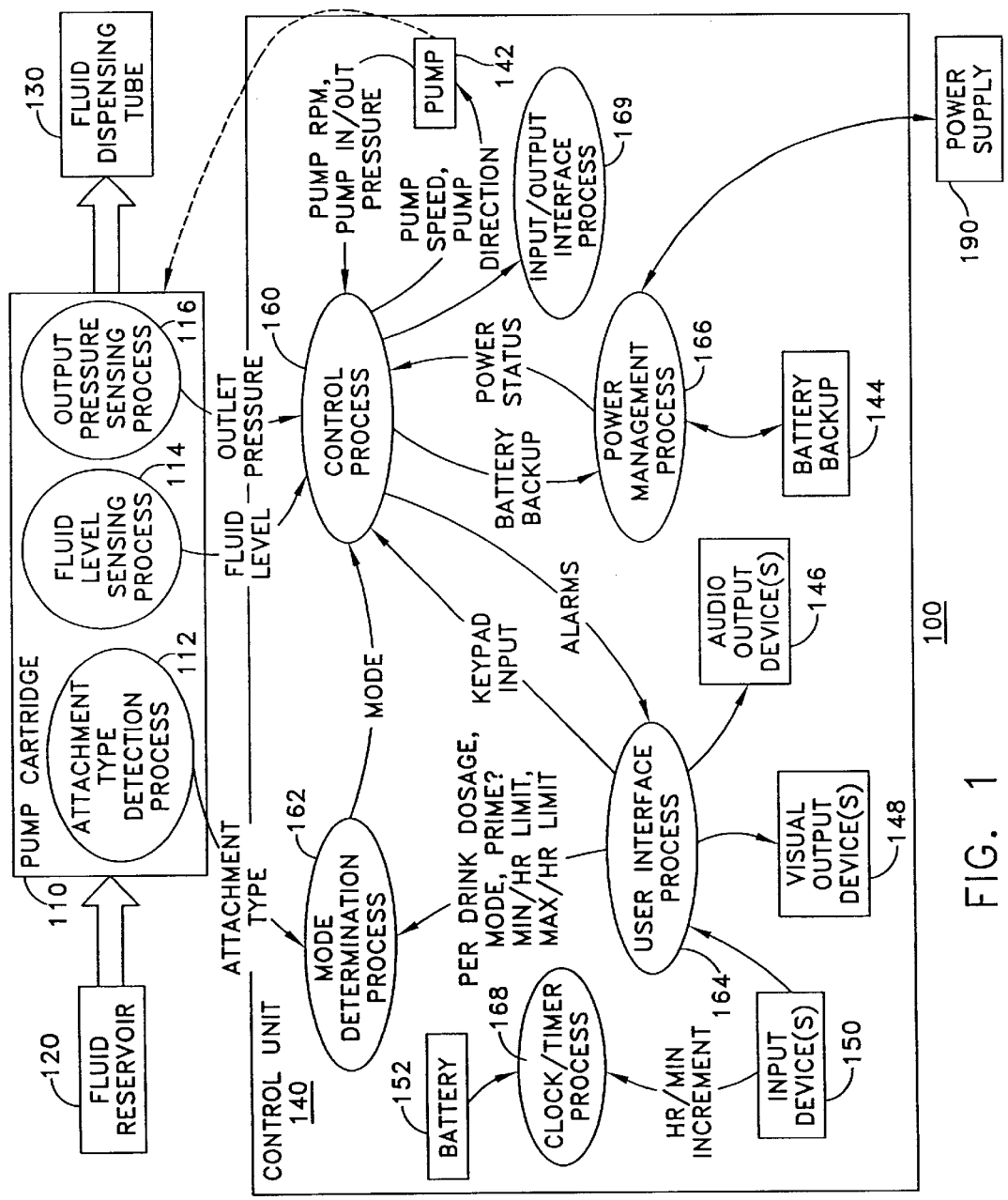
FIG. 1 is a high level diagram of processes that may be carried out by the present invention.

FIG. 1 is a high level diagram of subassemblies which may be included in the present invention and processes which may be carried out by those subassemblies. In FIG. 1, electrical or control signal paths are indicated with solid lines, fluid communication paths are indicated with stippled arrows, and a mechanical communication is indicated with a bold dashed line.

The fluid delivery system 100 of FIG. 1 may include four (4) basic subassemblies—namely a pump cartridge 110, a fluid reservoir 120, and a fluid dispensing tube 130, and a control unit 140. Note that although a power supply 190 is depicted as being separate from the control unit 140, it will be considered as a part of the control unit 140 in the following description. As shown in FIG. 1, the pump cartridge 110 is arranged, fluidically, between the fluid reservoir 120 and the fluid dispensing tube 130. Also, the pump cartridge 110 mechanically communicates with the pump 142 of the control unit 140.

As can be appreciated from FIG. 1, the control unit 140 is a major subassembly of the system 100. The control unit subassembly includes a pump 142, such as a peristaltic pump for example, a battery backup 144 to ensure uninterrupted power, an audio output device 146, such as a speaker or piezo-electric element for example, a visual output device 148, such as light emitting diodes and numeric displays for example, and an input device 150, such as a keypad and/or clock setting buttons for example. Though not shown in FIG. 1, the control unit 140 may also include a memory for storing parameter values and state information.

As can also be appreciated from FIG. 1, a number of processes, such as a control process 160, a mode determination process 162, a user interface process 164, a power management process 166, and a clock/timer process 168 for example, may be carried out by the control unit 140, and an input/output interface process 169. Each of these processes is introduced below and is described in more detail in §4.2.3 below.

The control process 160 may provide "pump speed" and "pump direction" control signals to the pump 142 and may accept "pump RPM", "pump inlet pressure" and "pump outlet pressure" values from the pump 142. The control process 160 may also accept "outlet pressure" and "fluid level" values from the pump cartridge 110, and a "mode" value from the mode determination process 162. The control process 160 may accept inputs from the user interface process 164 and may provide display values and alarm signals to the user interface process 164. Finally, the control process 160 may accept a "power status" signal from the power management process 166 and provide a "battery backup switchover" command to the power management process 166. An exemplary control process method 160' is described in §4.2.3.4 below with reference to FIG. 5.

The mode determination process 162, shown in FIG. 1, may accept an "attachment type" value from the pump cartridge 110 and may accept "per drink dosage", "mode", "prime?", "minimum/hour limit", and "maximum/hour limit" values from the user interface process 164. As introduced above, the mode determination process 162 may provide a "mode" value to the control process 160. An exemplary mode determination process method 162' is described in §4.2.3.2 below with reference to FIG. 3.

The user interface process 164, shown in FIG. 1, may accept inputs from input devices 150 and display values and alarms from the control process 160, and may provide keypad input indications to the control process, and outputs to the visual output device(s) 148 and the audio output device(s) 146. An exemplary user interface process method 164' is described in §4.2.3.3 with reference to FIG. 4.

The clock timer process 168, shown in FIG. 1, may be used by the other processes and basically maintains a time and can perform timing functions. This "system clock" may be maintained by a separate, replaceable battery 152, such as a lithium battery for example.

The input/output interface process 169 may implement communications protocol stacks for (i) accepting system parameters, (ii) accepting system software updates, (iii) accepting remote testing triggers, (iv) providing fluid delivery trend reports (such as, for example, historic data detailing flow rates, volumes, etc.), and/or (v) providing system test results. This process 169 may use a serial interface for example, such as an RS-232 interface. An exemplary input/output interface process method 169' is described in §4.2.3.5. below with reference to FIG. 20.

Finally, a power management process 166, shown in FIG. 1, may monitor states of a power supply 190 and a battery backup 144. As discussed above, process 166 may provide a power status message to the control process 160 and may receive a battery backup switchover command from the control process 160. In response to such a command, process 166 may control the power supply 190 and the battery backup 144. Alternatively, the power management process 166 may control the switchover itself and merely provide status messages to the control process 160. An exemplary power management process method 166' is described in §4.2.3.1 below with reference to FIG. 2.

Still referring to FIG. 1, the pump cartridge 110 may perform an attachment type detection process 112 for detecting the type of oral fluid dispenser 130 being used (or alternatively, may indicate an operating mode, such as negative pressure, positive pressure, or free flow for example), a fluid level sensing process 114 for monitoring the fluid level of the fluid reservoir 120, and an outlet pressure sensing process 116 for monitoring the fluid pressure at its outlet.

Having described the system 100 at a high level, a more detailed description of subassemblies which may be included in the system 100 is now provided in §4.2.2.

§4.2.2 Subassemblies and their Components

A detailed description of subassemblies which may be included in the system 100 is provided below. In particular, a control unit subassembly 140 is described in §4.2.2.1, pump cartridge subassemblies 110 are described in §4.2.2.2 and oral fluid dispenser subassemblies (or fluid dispensing tubes) 130 are described in §4.2.2.3. Note that the fluid reservoir subassembly 20 may include various types of containers such as plastic or glass bottles. That is, the present invention is designed to work with various types of known fluid containers. However, it is envisioned that the fluid reservoir 120 used may preferably hold from 12 to 16 ounces of fluid and should be sized so that the control unit 140 is not easily tipped (that is, maintains a low center of gravity) when it is fitted with the reservoir 120. Further, the fluid reservoir 120 may be provided with a removable bottom such that, when it is fitted (upside-down) into the control unit 140, the fluid reservoir 120 can be filled with more fluid or ice, for example, by removing the removable bottom. In any event, the fluid reservoir 120 may be provided with an adapter cap, described in §4.2.2.2 below, which is accepted by a fitting in the pump cartridge 110. In an alternative design, the reservoir may be provided with a tube extending into its interior such that it can be arranged, in various orientations, apart from the control unit 140.

§4.2.2.1 Control Unit

FIG. 7 is a perspective view of an exemplary embodiment of the control unit 140'. Physically, the control unit 140' is designed with a low center of gravity, preferably below split line 710. The external dimensions of the exemplary embodiment of the control unit 140' may be about five (5) inches wide by about nine (9) inches long and about five (5) inches high. The shell of the exemplary embodiment of the control unit 140' may be constructed of plastic injected molded pieces, and is preferably non-toxic, resistant to discoloration or chemical (for example, alcohol or disinfectant) decomposition. An area 720 for receiving the fluid reservoir 120 is also provided. As shown in the partially transparent perspective view of FIG. 8, a pump cartridge 110' is removably accommodated in the control unit 140' and includes an fitting 1130 for receiving the fluid reservoir 120. The reservoir may be provided with a valve cap and the fitting 1130 may include an actuator for opening the valve cap when the reservoir is properly seated. In this way, the reservoir 120 can be seated onto (and removed from) the fitting 1130 without fluid spills. Referring to both FIGS. 7 and 8, a control panel 730, to be described in more detail below, is provided.

FIG. 9 is a rear view of the exemplary embodiment of the control unit 140'. As shown in FIG. 9, the rear of the pump cartridge 110' is exposed at the rear of the control unit 140' and includes a tubing connection 910, such as a nipple for example. The control unit 140' includes a power switch 920, a power input port 925, a input/output interface port 930, such as a serial (e.g., RS232) port for example, and switches 940 for setting the hours and minutes of a system clock. Although not apparent in this view, the pump cartridge 110' overhangs the electrical components and switches of the control unit 140' such that any fluid spills may be diverted from these electrical components and switches. Alternatively, the control unit 140' may have an integral overhang.

FIG. 10 illustrates an exemplary keypad and display 730 which may be provided on the control unit 140'. A keypad portion, defined by keys 1012, 1020, 1032, 1042, 1050, and 1060, may be part of a fluid resistant, membrane switch. Each of the keys may include stainless steel domes for providing tactile feedback when a key is pressed. A beeper may provide audible feedback when a key is pressed. An alarm section 1010 further includes status LEDs 1014 through 1018, a limit section 1030 further includes status LEDs 1034 and 1036, and a drink mode section 1040 further includes status LEDs 1044 and 1046. A power LED 1070 may also be provided. A four (4) digit, seven (7) segment, alpha numeric display 1080 may be provided. Display type indicators 1082, 1084, 1086, and 1088 may be backlit "dead front" text messages.

Referring back to FIG. 1, the power supply 190 may serve to convert unregulated input power from a wall mount power supply into regulated voltage levels (such as +12 volt @ 1 amp for example) used by the various electrical circuits and the pump of the system 100. A wall mounted power supply 190 may provide electrical isolation (such as 4000 volts for example) from the AC power input. (Pressure transducers in the pump cartridge may provide additional electrical isolation, such as 1500 volts of isolation for example.)

A battery backup 144 may be provided with a trickle charge as needed. The battery backup 144 may even be charged when the power switch 920 has been turned off. The battery pack 144 may provide four (4) hours of backup power in the event of AC power failure. The battery pack 144 may be user replaceable and may be accessed via the underside of the control unit 140'.

The control unit 140' may also house a pump 142 (not shown), such as a peristaltic pump with a gear reduction assembly and a multi-roller pump head for example.

§4.2.2.2 Pump Cartridge

FIGS. 11A and 11B provide two perspective, partially transparent views of an exemplary embodiment of the pump cartridge 110'. As shown in these Figures, a reservoir 120' is held by fitting 1130. Fluid from the reservoir 120' will flow through pump tubing 1125 which is provided against a curved wall 1120. The roller head of a peristaltic pump (not shown) will extend through the opening 1110 defined in the pump cartridge 110' such that the rollers of its head engage the pump tubing 1125. Recall from FIG. 9 that the rear of the pump cartridge 110' may include a tubing connection 910, such as a nipple for example. Referring to FIG. 11A, a fluid level sensor 1140 may be provided. This sensor 1140 may inform the control unit 140 when there is only one (1) to two (2) inches of fluid remaining in the reservoir for example. This sensor 1140 may be used to perform the fluid level sensing process 114 depicted in FIG. 1. Referring to FIG. 11B, an outlet pressure sensor 1150 may be provided. This sensor 1150 may be used to perform the outlet pressure sensing process 116 depicted in FIG. 1. The pump cartridge 110' may include a quick disconnect electrical (or optical or mechanical) connection, such as conductive pad contacts for example, for passing signals from the sensors 1140 and 1150 to the control unit 140'.

The pump cartridge 110' may detect physical, optical, or electrical or conductive contacts on a connected fluid dispensing tube 130 to at least determine whether the fluid dispensing tube is intended to operate in a negative or positive pump pressure mode, and perhaps to identify the exact type of fluid dispensing tube 130 attached.

An alternative pump cartridge 110" is depicted in FIGS. 21A through 21H and 22. More specifically, FIG. 21A is a plan view, FIG. 21B is an end view, FIG. 21C is a perspective view, FIG. 21D is a side view, and FIG. 22 is a partial transparent perspective view of the alternative pump cartridge 110". The alternative pump cartridge 100" basically includes a shell, defined by side walls 2192 and 2194, front wall 2196, rear wall 2198, and floor 2190, and tubing 2125. Within the shell, a cartridge reservoir is defined by floor 2190, side wall 2192, front wall 2196, rear wall 2198, nipple wall 2193, and internal wall 2199. The cartridge reservoir is covered (by a cover not shown).

Referring to FIGS. 21E through 21H, 23, 24A, and 24B, when an adapter cap 2400/2400' of a reservoir is placed onto a fitting 2130, a projection 2170 of the fitting 2130 opens a valve normally biased closed and fluid from the reservoir flows into the cartridge reservoir.

More specifically, as shown in FIGS. 21E through 21H and FIG. 23, the pump cartridge 110" (or 110') may include a fitting 2130 (or 1130) for accepting a reservoir having an adapter cap 2400/2400' (described below). The fitting 2130 includes a cup portion defined by a cylindrical wall 2172 and a floor 2173. An opening 2171 is defined in a portion of the floor 2173 arranged over the projection 2170. Below the cup portion is a skirt 2174 having flow openings 2175.

FIGS. 24A and 24B are cross-sectional side views of a cup adapter 2400/2400'. The end of a reservoir, such as a threaded bottle for example, is fit into cylindrical section 2405. When the cup adapter 2400/2400' is pushed into the cylindrical opening 2172 of the fitting 2130, a plunger seat 2430 passes through the opening 2171 and is engaged by the projection 2170. The value seat 2410, which is normally biased closed by spring 2120 is opened and fluid flows from the reservoir, out the valve opening, through openings in a skirt 2440 of the cup adapter 2400/2400', through opening 2171 and through flow openings 2175 in the skirt 2174 of the fitting 2130, into the cartridge reservoir. As shown in FIG. 24B, the cap adapter 2400' may include guides 2450, such a posts for example, for guiding the movement of the plunger seat 2430. Fluid then can enter tubing 2125 via an opening in the nipple wall 2193 and nipple 2180. The tubing 2125 will have been snuggly fit, for example by stretching, around rollers of a peristaltic pump (not shown). When the peristaltic pump is activated, fluid will be drawn from the cartridge reservoir and will exit at a port at the rear wall 2198 of the cartridge 100". (Recall, e.g., the outlet 910 of FIG. 9.)

An exemplary assembly 2140, provided in the cartridge 110", for determining a low fluid level condition is now described. Basically, the assembly 2140 includes a light transmission part 2142 (such as a multifaceted prism for example), a light blocking part 2146 (such as a floatable ball for example), a light receiving part 2144 (such as a prism for example), and a containment wall (only a part of which is shown) 2148 for containing lateral movement of the light blocking part 2146. A light source (not shown), such as an LED for example, provided in the control unit 140 emits light into the prism 2142 and a light sensor (not shown), such as a photo-conductive element for example, provided in the control unit 140 collects light from the prism 2144. The first prism 2142 is arranged to direct light towards the second prism 2144. If the cartridge reservoir is full, the light blocking element 2146 contained by the walls 2148 and the prisms 2142, 2144, will float, thereby blocking light emitted from the first prism 2142 from entering the second prism 2144. However, when the cartridge reservoir is empty (or almost empty), the light blocking element 2146 will drop, thereby enabling light emitted from the first prism 2142 to be detected by the second prism 2144. Thus, when the light sensor associated with the second prism 2144 detects light, a low reservoir level is inferred. Naturally, this level sensing arrangement 2140 might not be suitable for use with relatively opaque fluids.

In one embodiment, the prism 2142 can be provided with additional facets for directing light towards prisms 2160A and 2160B. The control unit 140 may include further light sensors, each associated with one of the prisms 2160A and 2160B. Different cartridges may be provided for dispensers having different flow characteristics, such as negative flow, positive flow, and free flow for example. Such different cartridges may be provided with either one, or both of the additional prisms 2160A and 2160B. Thus, for example, a positive flow cartridge may include both prisms 2160A and 2160B such that the additional light sensors of the control unit 140 detect light (indicating a positive flow), a negative flow cartridge may include only prism 2160A such that only one of the additional light sensors of the control unit 140 detects light (indicating a negative flow), and a free flow cartridge may include only prism 2160B such that only the other one of the additional light sensors of the control unit 140 detects light (indicating a free flow).

A pressure transducer 2150 may measure the pressure in the tube exiting the cartridge 110".

Either of the pump cartridges 110' or 110" may include an expansion chamber (not shown), such as a stretchable bladder having shape memory for example, so that pressure can build in the cartridge and drops in pressure may be sensed by the sensor by outlet pressure sensor 1150 or 2150. Naturally, if the tubing of the dispenser 120 has a sufficient coefficient of expansion and shape memory, such an expansion chamber need not be provided.

Either of the pump cartridges 110' or 110" may also include a valve built into its outlet so that if a fluid dispensing tube 130 is disconnected, no fluid will leak from the outlet 910 of the pump cartridge 110' or 110".

Finally, fluid filtration means (not shown) may be provided in the pump cartridge 110' or 110" (and/or the reservoir valve cap, and/or the fluid dispensing tube 130).

§4.2.2.3 Oral Fluid Dispensers

FIGS. 12A through 19 depict various types of oral fluid dispensers. In each case, these dispensers may include, or may be connected to, a short section (such as four (4) feet, for example) of tubing having a distal end connected with the tubing connection 910 of the pump cartridge 110'. Each of the presently contemplated oral fluid dispensers is now described. However, as can be appreciated by one skilled in the art, other oral fluid dispensers may be used with the other components of the present invention.

FIG. 12A is a perspective view, and FIG. 12B is a partial transparent perspective view, of a sip tip oral fluid dispenser 1200 which may be used by the present invention. As shown in these Figures, the sip tip oral fluid dispenser 1200 includes a proximal end 1210, a distal end 1220, and may include a check valve 1230. This dispenser 1200 functions as does a simple straw; fluid is obtained by a sucking action at the proximal end 1210. The check valve 1230 reduces the possibility of fluid leakage and/or back flow.

FIG. 13A is a perspective view, and FIG. 13B is a partial transparent perspective view, of a pump swab tip oral fluid dispenser 1300 which may be used by the present invention. As shown in these Figures, the pump swab tip oral fluid dispenser 1300 includes a swab tip 1320 at its proximal end. The material forming the swab tip 1320 should be soft and absorbent, or sponge like, so that it can retain water. Fine control of water quantity is provided by the pump actuator 1330 which is an exposed area of a soft inner bladder. A first check valve 1350 may be provided at the proximal end of the dispenser 1300, while a second check valve 1340 may be provided at the distal end 1310 of the dispenser 1300. Thus, the pump swab tip oral fluid dispenser 1300 may be used to wet the lips of a user with small amounts of water. This fluid dispenser 1300 may be provided with a shorter distance between the pump actuator 1330 and the swab tip 1320 for wetting a user's lips, or a longer distance between the pump actuator 1330 and the swab tip 1320 for moistening the inside of a user's mouth.

FIG. 14A is a perspective view, and FIG. 14B is a partial transparent perspective view, of a swab tip oral fluid dispenser 1400 which may be used by the present invention. This fluid dispenser 1400 is similar to the pump swab tip oral fluid dispenser 1300 in that is has a soft tip 1420 at its proximal end. However, a valve 1440 and valve actuator 1430 are provided rather than a soft bladder and pump 1330. Thus, when the valve actuator 1430 is pressed, water begins to flow to the surface of the soft swab tip 1420, until the valve actuator 1430 is released. Like the pump swab tip oral fluid dispenser 1300, the swab tip oral fluid dispenser 1400 may be provided with a shorter distance between the pump actuator 1430 and the swab tip 1420 for wetting a user's lips, or a longer distance between the pump actuator 1430 and the swab tip 1420 for moistening the inside of a user's mouth.

FIG. 15A is a perspective view, and FIG. 15B is a partial transparent perspective view, of a bite valve oral fluid dispenser 1500 which may be used by the present invention. A bite valve actuator 1520 opens valve 1530 when a user bites downs on it. Fluids enter at the distal end 1510 of the dispenser 1500. Thus, the bite valve oral fluid dispenser 1500 may be used to provide a continuous flow of fluid when a user bites down on the actuator 1520. When the user stops biting, the fluid flow ceases.

FIG. 16A is a perspective view, and FIG. 16B is a partial transparent perspective view, of a drink straw oral fluid dispenser 1600 which may be used by the present invention. In this dispenser 1600, a valve actuation button 1640 is provided between the proximal 1620 and distal 1610 ends. When the value actuation button 1630 is pressed, the valve 1640 opens. Thus, the operation of this dispenser 1600 is similar to that of the bite valve oral fluid dispenser 1500, except that a user presses a button valve actuator 1630, rather than biting a bite value actuator 1520.

FIG. 17A is a perspective view, and FIG. 17B is a partial transparent perspective view, of a squeezer oral fluid dispenser 1700 which may be used by the present invention. This dispenser 1700 includes a squeezable bladder 1730, which may be held in a user's hand, for allowing a user to pump water through check valve 1750 to the proximal end 1720. A second check valve 1740 is provided at the distal end 1710. The squeezable bladder 1730 may be about three (3) to six (6) inches long, for example, and may hold about 15 to 30 ml of fluid for example.

FIG. 18A is front perspective view, and FIG. 18B is a rear perspective view, of a bedside cup attachment oral fluid dispenser 1800 which may be used by the present invention. This dispenser 1800 permits a user to fill a small cap, such as a standard 2.5 ounce "dixie" type cup 1870 for example, at his(her) bed. The dispenser 1800 is "C-shaped" and defines a hood 1820 and a cup holder 1880. A button 1840 (which operates a valve—not specifically shown) is provided on the dispenser 1800, and in this exemplary embodiment, on the hood 1820, and allows the user to refill the cup 1870 with fluid. A fluid delivery tube 1860 is, in this exemplary embodiment, attached to the rear of the dispenser 1800. Finally, a clamp 1830 permits the dispenser to be removably fixed to a bed rail 1810. Although not shown, the cup holder 1880 may include a drain for draining any spilled fluid or fluid inadvertently dispensed into a full cup 1870 or inadvertently dispensed when a cup 1870 is not situated in the holder 1880. In an alternative embodiment, the bedside cup attachment oral fluid dispenser 1800 may be placed on a bedside table and need not include the clamp 1830. In such an embodiment, the supply tube 1860 would preferably extend roughly parallel to the bottom surface of the dispenser 1800 and the dispenser 1800 would preferably be weighted to have a low center of gravity.

FIG. 19 is a perspective view of a tube cup oral fluid dispenser 1900 which may be used by the present invention. This dispenser 1900 offers similar features as the bedside cup attachment oral fluid dispenser 1800, but further permits a user to refill the cup 1960 without returning it to its holder 1920. That is, the tube 1930 can be removed from its holster 1925. The holster 1925 includes a water refilling button 1940 which, when pressed, presses a valve actuator (not shown) on the tube 1930. A hanger member 1910, attached to the cup holder 1920, may be hung form a bed rail 1950. In a first alternative embodiment, the cup holder 1920 could have a reduced inner diameter than that of a top of the cup so that the top of the cup 1960 could be easily grasped by the user. Further, the tube holster 1925 may be extended upward so that the curved section of the tube 1930 would be at least a cup's length above the top of the cup holder 1920. In this way, a user could more easily remove the cup 1960 without inadvertently hitting the curved end of the tube 1930. As can be appreciated by one skilled in the art, this embodiment could be modified to sit on a bedside table.

§4.2.3 Exemplary Methods for Subcomponent Processes

Below, the exemplary methods which may be used to carry out the various processes introduced above, are described. These methods may be effected by the execution of stored instructions by a processor. More specifically, referring to FIG. 6, a system 600 may include a bus or network 610 coupled with a processor(s) 620, a storage device(s) 630 and an input/output interface(s) 640. The storage device(s) 630 may include flash memory. In this way, stored instructions may be updated in the field. The input/output interface(s) 640 may include an RS-232 serial port. In this way, the stored instructions may be updated, or new instructions may be directly provided, from an external source, and information, such as trend information for example, may be uploaded to an external system for analysis. The processor(s) 620 may be a low-power general purpose microprocessor, or an application specific integrated circuit (or "ASIC") for example.

Having described a system 600 which may be used to effect the processes, exemplary methods which may be used to carry out the processes are now described below. First, an exemplary power management process method is described in §4.2.3.1. Second, an exemplary mode determination process method is described in §4.2.3.2. Third, an exemplary user interface process method is described in §4.2.3.3. Fourth, an exemplary control process method is described in §4.2.3.4. Finally, an exemplary input/output interface process is described in §4.2.3.5. Note that the methods described and the operations that they perform are exemplary; in some cases, operations from different methods can be combined under a single method, operations from a single method can be separated and performed by separate methods, or operations performed one method may be performed by a different method than the one illustrated. Similarly, in some cases, a process can be carried out in a subassembly other than the one illustrated.

§4.2.3.1 Power Management Method

Figure 2:
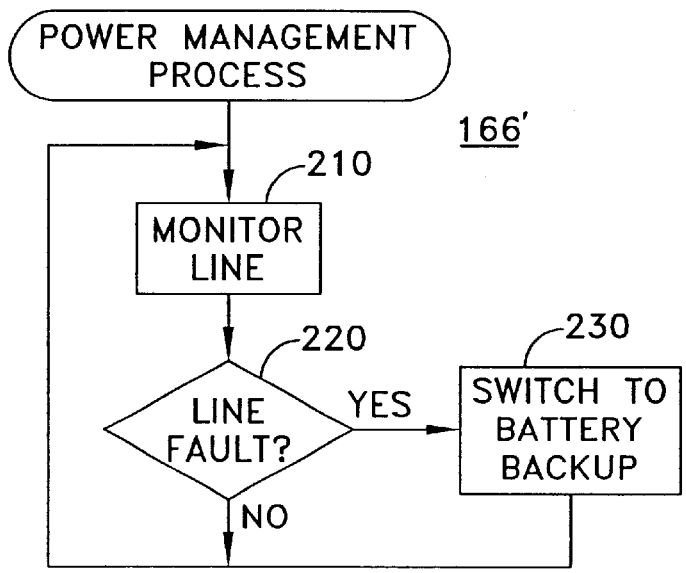
FIG. 2 is a high level flow diagram of an exemplary power management process method which may be performed by a control unit of the present invention.

FIG. 2 is a flow diagram of an exemplary power management process method 166'. As shown in step 210, the line (that is, power coming in from the power supply 190) is monitored. As shown in decision step 220 and step 230, if a fault is detected, the power supply source is switched to a battery backup. In one embodiment of the present invention, referring back to FIG. 1, the power management process may either directly, or via the control process 160, inform the user interface process 164 that battery power is being used. In response, the user interface process 164 may enter a low power operating mode in which the visual outputs 148 are blanked after a period of keypad inactivity.

§4.2.3.2 Mode Determination Method

Figure 3:
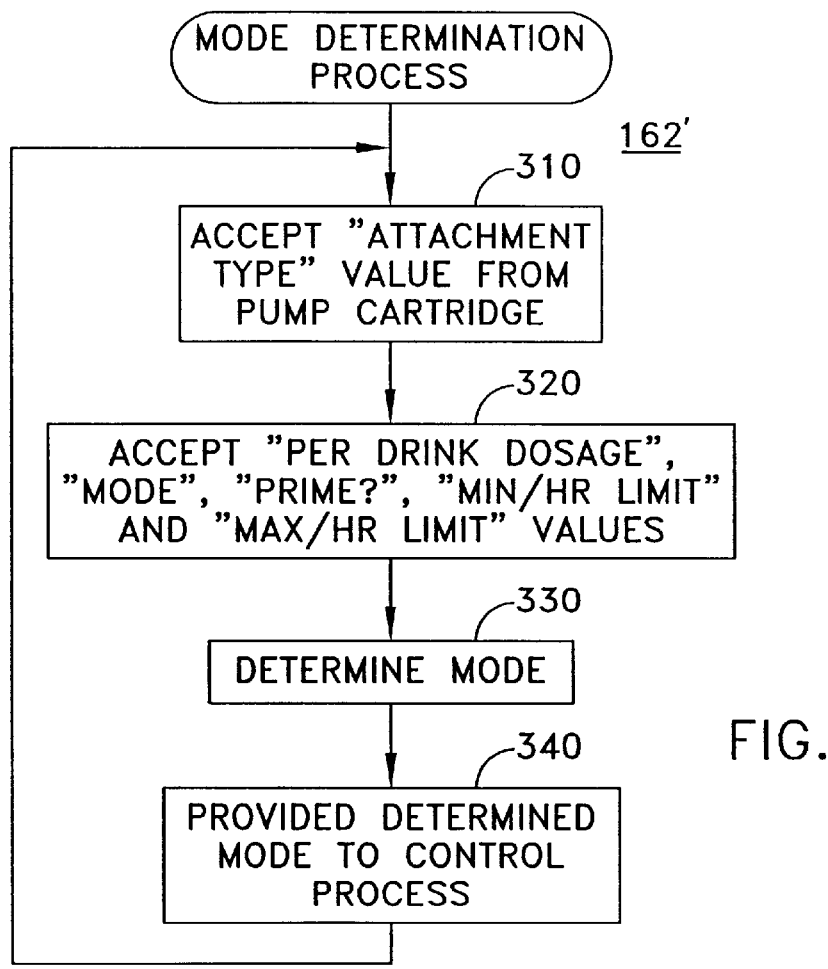
FIG. 3 is high level flow diagram of an exemplary mode determination process method which may be performed by a control unit of the present invention.

FIG. 3 is a flow diagram of an exemplary power management process method 162'. As shown in step 310, the mode determination process accepts an "attachment type" value from the pump cartridge 110. (See, e.g., FIG. 1.) Also, as shown in step 320 shown in FIG. 3, "per drink dosage mode", "prime?", "min/hr limit", and "max/hr limit" values are accepted from the user interface process 164. (See, e.g., FIG. 1.) Next, as shown in step 330 shown in FIG. 3, a mode is determined based on at least some of the accepted values listed above. Finally, as shown in step 340, the "mode" value determined is provided to the control process 160. (See, e.g., FIG. 1.)

§4.2.3.3 User Interface Method

FIG. 4, which includes FIGS. 4A through 4G, is a flow diagram of an exemplary user interface process method 164. As shown in decision step 401, it is determined whether a reservoir low alarm has been received (either directly from the fluid level sensing process 114, or via the control process 160). If so, the "reservoir" LED 1018 is lit as shown in step 402. An audible alarm may also sound. Next, in decision step 403, it is determined whether the reservoir has been replaced or refilled. If so, the alarm is cleared (and the "reservoir" LED 1018 is extinguished) as shown in step 404 and processing continues to decision step 405. Otherwise, processing continues directly to decision step 405. Returning to decision step 401, if a reservoir low alarm is not received, processing continues directly to decision step 405.

At decision step 405, it is determined whether the battery backup 144, rather than power supply 190, is providing power (either directly from the power management process 166, or via control process 160). If so, the "battery" LED 1016 is lit as shown in step 406. An audible alarm may also sound. Next, in decision step 407, it is determined whether the AC power, from power supply 190, has been restored. If so, the alarm is cleared (and the "battery" LED 1016 is extinguished) as shown in step 408 and processing continues, via node A 409, to decision step 410. Otherwise, processing continues, via node A 409, to decision step 410. Returning to decision step 405, if the battery backup 144 is not being used, but rather, the power supply 190 is being used, processing continues, via node A 409, to decision step 410.

At decision step 410, it is determined whether the min/hour dosage or max/hour dosage thresholds have been met (from control process 160). If so, the "limits" LED 1014 is lit as shown in step 411. An audible alarm may also sound. Next, in decision step 412, it is determined whether the alarms key 1012 has been pressed (to clear this alarm condition). If so, the alarm is cleared (and the "limits" LED 1014 is extinguished) as shown in step 413 and processing continues to decision step 414. Otherwise, processing continues directly to decision step 414. Returning to decision step 410, if the min/hour or max/hour dosage thresholds are not met, processing continues directly to decision step 414.

At decision step 414, it is determined whether a hardware or software failure has been detected (from control process 160). If so, the "system" LED 1015 is lit as shown in step 414. An audible alarm may also sound. Next, in decision step 416, it is determined whether the system or hardware failure is due to a spurious failure. If so, the alarm is cleared (and the "system" LED 1016 is extinguished) as shown in step 417 and processing continues, via node B 418, to decision step 419. Otherwise, processing continues, via node B 418, to decision step 419. Returning to decision step 414, if no hardware or software error is detected, processing continues, via node B 418, to decision step 419.

At decision step 419, it is determined whether the output button 1020 is being pressed. If not, processing continues, via node C 426, to decision step 427. If, on the other hand, it is determined that the output button 1020 is being pressed, the total amount of fluids consumed (in a most recent time period) is displayed on numeric display 1080 and the mL indicator 1083 is backlit. Next, as shown in decision step 421, it is determined whether the output button 1020 is pressed again within a short predetermined time, such as three (3) seconds for example. If so, the elapsed time corresponding to the volume consumed is displayed on numeric display 1080 and the "elapsed" indicator 1084 is backlit. Next, as shown in decision step 423, it is determined whether the output button 1020 is pressed again within a short predetermined time, such as three (3) seconds for example. If so, processing continues back to step 420. If not, or, returning to step 421, if the output button was not pressed again within the short predetermined time, such as three (3) seconds for example, processing continues to decision step 424. As shown in decision step 424, if the output button 1020 is not pressed again within a longer predetermined time, such as one (1) minute for example, processing continues, via node C 426, to decision step 427. If, on the other hand, the output button 1020 is pressed again within the longer predetermined time, such as one (1) minute for example, the time and volume data is cleared (and the associated LED is extinguished) as shown in step 425, and processing continues, via node C 426, to decision step 427.

At decision step 427, it is determined whether or not the "drink mode" button 1042 is pressed. If so, processing branches to decision step 428 where it is determined whether a current mode is a "control" mode or a "normal" mode. Basically, as will be apparent from the following description, pressing the drink mode serves to toggle the mode between "control" and "normal". If the current mode was "control", the "normal" mode is entered as shown in step 429. In this mode, the display 1080 indicates a predetermined fluid dosage, such as 30 ml for example, as shown in step 430. Finally, the "normal" LED 1044 is lit and the "control" LED 1046 is extinguished. Processing then continues to decision step 450.

Returning now to decision step 428, if the current mode was determined to be the "normal" mode, the "control" mode is entered as shown in step 432. Next, as shown in step 433, the "normal" LED 1044 is extinguished and the "control" LED 1046 is lit. Next, as shown in step 434, the current dosage value is flashed on display 1080. If, as shown in decision steps 435 and 436, and step 437, an up arrow key 1050 is depressed (hit) within a predetermined time period, such as one (1) minute for example, the dosage is incremented (by a predetermined amount such as 1 ml or 10 ml for example), and processing returns to step 434. Alternatively, the longer the up arrow key 1050 is depressed, the faster the dosage value will be incremented. If, as shown in decision steps 435, 436 and 438, and step 439, a down arrow key 1050 is hit within a predetermined time period, such as one (1) minute for example, the dosage is decremented, and processing returns to step 434. Alternatively, the longer the down arrow key 1050 is depressed, the faster the dosage value will be decremented. Returning to step 435, if neither arrow key is depressed within the predetermine time period, such as one (1) minute for example, processing continues to decision step 450. Returning to step 427, if the "drink mode" button is not being depressed, then processing continues directly to decision step 450.

At decision step 450, it is determined whether the "prime" button 1060 is being depressed. If so, the pump 142 is run until the "prime" button 1060 is released, at which time processing continues, via node D 452, to decision step 453. Returning to decision step 450, if the "prime" button 1060 is not being depressed, processing continues, via node D 452, to decision step 453.

At decision step 453 it is determined whether or not the "limit/hr" button 1032 is being depressed. If so, processing proceeds to decision step 454 where it is determined whether the current limit is min(minimum) or max(maximum). If the current limit was determined to be the "min" mode, the "max" mode is entered as shown in step 455. Next, as shown in step 456, the "min" LED 1036 is extinguished and the "max" LED 1034 is lit. Next, as shown in step 457, the current dosage value is flashed on display 1080. If, as shown in decision steps 458 and 459, and step 460, an up arrow key 1050 is hit within a predetermined time period, such as one (1) minute for example, the dosage is incremented (by a predetermined amount such as 1 ml or 10 ml for example), and processing returns to step 457. Alternatively, the longer the up arrow key 1050 is depressed, the faster the dosage value will be incremented. If, as shown in decision steps 458, 459 and 461, and step 462, a down arrow key 1050 is hit within a predetermined time period, such as one (1) minute for example, the dosage is decremented, and processing returns to step 457. Alternatively, the longer the down arrow key 1050 is depressed, the faster the dosage value will be decremented. Returning to step 458, if neither arrow key 1050 is pressed within the pre-determine time period, such as one (1) minute for example, processing continues, via node E 471, to decision step 472.

Returning to decision step 454, if the current limit value is "max" mode, the "min" mode is entered as shown in step 463. Next, as shown in step 464, the "max" LED 1034 is extinguished and the "min" LED 1036 is lit. Next, as shown in step 465, the current dosage value is flashed on display 1080. If, as shown in decision steps 466 and 467, and step 468, an up arrow key 1050 is hit within a predetermined time period, such as one (1) minute for example, the dosage is incremented (by a predetermined amount such as 1 ml or 10 ml for example), and processing returns to step 465. Alternatively, the longer the up arrow key 1050 is depressed, the faster the dosage value will be incremented. If, as shown in decision steps 466, 467 and 469, and step 470, a down arrow key 1050 is hit within a predetermined time period, such as one (1) minute for example, the dosage is decremented, and processing returns to step 465. Alternatively, the longer the down arrow key 1050 is depressed, the faster the dosage value will be decremented. Returning to step 466, if neither arrow key 1050 is depressed within the pre-determine time period, such as one (1) minute for example, processing continues, via node E 471, to decision step 472.

Returning to step 453, if the "limit per hour" button 1032 was not pressed, then processing continues, via node E 471, to decision step 472.

At decision step 472, it is determined whether or not a clock set hour button 940 is being pressed. If so, as shown in step 473, the time is displayed on display 1080 and the "time" panel 1088 is backlit. In decision step 474, it is determined whether the down arrow key 1050 is depressed and the clock set hour key 940 is still depressed. If so, as shown in step 475, the hour is decremented. If not, processing continues to decision step 476. In decision step 476, it is determined whether the up arrow key 1050 is depressed and the clock set hour key 940 is still depressed. If so, as shown in step 477, the hour is incremented. If not, processing continues to decision step 478. Returning to decision step 472, if the clock set hour button is not being depressed, processing continues directly to decision step 478.

At decision step 478, it is determined whether or not a clock set minute button 940 is being depressed. If so, as shown in step 479, the time is displayed on display 1080. In decision step 480, it is determined whether the down arrow key 1050 is depressed and the clock set minute key 940 is still depressed. If so, as shown in step 481, the minute is decremented. If not, processing continues to decision step 482. In decision step 482, it is determined whether the up arrow key 1050 is depressed and the clock set minute key 940 is still depressed. If so, as shown in step 483, the hour is incremented. If not, processing continues, via node F 484, to decision step 485. Returning to decision step 478, if the clock set minute button is not being depressed, processing continues, via node F 484, to decision step 485.

At decision step 485, it is determined whether it is time to replace (or clean) any fluidic component or components (such as a dispenser 130 or the pump cartridge 110. If so, as shown in step 486, a cleaning LED 1017 is lit and an audible alarm may be provided. Next, as shown in step 487, it is determined whether or not the alarms button 1012 was depressed or the relevant fluidics component was replaced. If so, the alarm is cleared (and the cleaning LED 1017 is extinguished), as shown in step 488, and processing continues to return node 489. If not, processing continues directly to return node 489. Returning to decision step 485, if it is determined that it is not yet time to replace (or clean) a fluidic component or components, processing continues directly to return node 489.

§4.2.3.4 Control Method

FIG. 5 is a flow diagram of an exemplary control process method 160'. As shown in step 510, the process accepts an "outlet pressure" value from the pump cartridge 110, as well as "pump RPM", "inlet pressure" and "outlet pressure" values from the pump 142, and the "mode" value from the mode determination process 162. (See, e.g., FIG. 1.) Next, as shown in step 520 in FIG. 5, "pump speed" and "pump direction" values are determined based on some or all of the above-mentioned accepted values. As shown in step 530, the "pump speed" and "pump direction" values are provided as commands to the pump 142. In step 540, the fluid level value is accepted from the pump cartridge. As shown in decision step 550, it is determined whether a "fluid level" value accepted is below a predetermined threshold. In an alternative method, this determination may be made by the fluid level sensing process 114 itself. In any event, if the fluid level is below the predetermined(min) threshold, as shown in step 560, an appropriate alarm signal is provided to the user interface process 164. Further, as shown in step 570, a "line power status" value is accepted from the power management process 166. If the status of the line power is not acceptable, the control process may instruct the power management process 166 to switch over to battery power as shown in step 590. As discussed above, in an alternative method, the power management process 166 may make a switch over determination itself and merely inform the control process 160 when it has done so.

The control process 160 may also perform a variety of self tests, for example during power up and periodically or continuously during operation. Such self tests may include battery voltage monitoring, system memory tests, data acquisition tests, pressure sensor tests, LED and display tests, processor integrity tests, and stuck keyboard switch tests, for example. Naturally, these tests may be distributed to other processes which may provide their results back to the control process 160. If a failure is detected, the user interface process 164 may be informed. (Recall decision step 414 of the exemplary user interface process method 164'.)

§4.2.3.5 Input/Output Interface Method

FIG. 20 is a flow diagram of an exemplary input/output interface process method 169'. As shown in decision step 2010 and step 2015, if a test trigger has been received, this trigger may be passed to the control process 160 for performing or initiating some sort of system test. Next, as shown in decision step 2020 and step 2025, if test results are provided to the input/output interface process 169, it may upload those test results to a remote monitor. The remote monitor is a device other than the fluid delivery system and therefore may be a local computer or a remote computer for example. Next, as shown in decision step 2030 and step 2035 if a trend report is provided from the system, such a report may be uploaded to a remote monitor. Finally, as shown in decision steps 2040 and 2042, if new software, or a notification of the availability of new software, is received from a remote source, the user may be notified, for example via the control process 160 and user interface process 164. As shown in decision step 2044 and step 2046, if the user accepts the new software, the update is downloaded and may be provided to the control process 160. Naturally, in an alternative method, new software can be downloaded and implemented automatically, without the need for user approval. The method 169' is exited via return node 2050.

Having described exemplary subassemblies and methods that can be carried out by such subassemblies, an example of an operation of the present invention is now provided in §4.3 below.

§4.3 Example of Operation

The exemplary embodiment of the present invention operates as follows. A pump cartridge 110' is placed in the control unit 140' as shown in FIG. 8. A fluid reservoir 130' (which may have an adapter cap 2400/2400') is positioned through the opening 720 and is engaged with the fitting 1130 (or 2130). Referring to FIG. 9, the power switch 920 is turned on. The distal end of one of the oral fluid dispensers, or the distal end of a tube section connected with one of the oral fluid dispensers, is attached to connector 910. The priming button 1060 is pushed. In response, the pump motor turns, its rollers engaging the pump tubing 1125 (or 2125) of the pump cartridge 110' (or 110"), thereby pushing air out of the system and drawing fluid from the reservoir 120'. When the system is filled with fluid, the user may draw fluid from the system, either by sucking on the end 1210 of the sip tip oral fluid dispenser 1200, pressing on the bladder 1330 of the pump swab tip oral fluid dispenser 1300, pressing the valve actuator 1430 of the swab tip oral fluid dispenser 1400, biting the bite valve actuator 1520 of the bite valve oral fluid dispenser 1500, pressing the button valve actuator 1630 of the drink straw oral fluid dispenser 1600, squeezing the squeezable bladder 1730 of the squeezer oral fluid dispenser 1700, pressing the button 1840 of the bedside cup attachment oral fluid dispenser 1800, or by pressing the button 1940 of the tube cup oral fluid dispenser 1900.

Referring to FIGS. 11, 21A–21H and 1, the outlet pressure sensor 1150 (or 2150) performs an outlet pressure sensing process 116 to provide an outlet pressure to a control process 160. Based on the outlet pressure, as well as a mode value, the control process 160 provides pump speed and/or pump direction commands to the pump 142.

The following table summarizes the fluid delivery modes of the system of the present invention.

|  | SIP TIP | PUMP SWAB | BITE VALVE | DRINK STRAW | SQUEEZER | BEDSIDE CUP | TUBE CUP | SWAB |
|---|---|---|---|---|---|---|---|---|
| OPER. BUTTON REQ'D.? | NO | YES (BLADDER) | NO | YES | YES (BLADDER) | YES | YES | YES |
| OUTLET CHECK VALVE PROV'D.? | YES | YES | YES (BITE VALVE) | YES (BUTTON VALVE) | YES | NO | NO | YES |
| BLADDER? | NO | NO | NO | NO | YES | YES (INTERNAL) | YES (EXTERNAL) | NO (EXTERNAL) |
| PUMP PRES. MODE | NEG. | NEG. | POS. | POS. | NEG. | POS. | POS. | POS. |
| INIT. USE BY: | SUCK | PUMPING | BITING | PRESS BUTTON | PUMPING | PRESS BUTTON | PRESS BUTTON | PRESS BUTTON |
| CHECK VALVE FOR BACK-FLOW PREVENT? | NO | YES | NO | NO | YES | NO | NO | NO |
| PER-DRINK OPER'N MODE | NORMAL AND CONTROL | NORMAL | NORMAL AND CONTROL | NORMAL AND CONTROL | NORMAL AND CONTROL | NORMAL AND CONTROL | NORNAL AND CONTROL | CONTROL |

As can be appreciated from the foregoing table, the system of the present invention may use two (2) basic parameters—namely dispenser (or tip) type, and a selected "drink mode"—for determining the its mode of operation. Further, the various dispenser (or tip) types disclosed operate with a positive fluid pressure or a slight negative fluid pressure.

§4.4. Conclusions

The present invention provides a system for delivering fluids which includes a pump (such as a peristaltic pump for example), a pump cartridge, a fluid reservoir, and a variety of fluid dispensers, including oral fluid dispensers. By providing a number of oral fluid dispensers, the one best suited for the needs of a particular application can be selected. The pump cartridge and/or the fluid dispensers are disposable. The operation of the pump may be controlled based, at least in part, on the type of fluid dispenser being used. Further, a selectable mode can be used to further control the operation of the pump.

By providing methods and apparatus for monitoring the amount of fluids delivered over given periods of time, the present invention may provide a reminder (such as an audio and/or visual alarm for example) if too much or too little fluid is delivered (and presumably consumed). The thresholds for such alarm conditions may be set and modified by a user.

The present invention also provides methods and apparatus for monitoring the state of the fluid delivery system itself, and monitoring trends in fluid delivery.

What is claimed is:

1. In a system for delivering fluids via an oral dispenser to a patient, the oral dispenser being connected through a fluid delivery tube to a pumping station, the method comprising the steps, performed at the pumping station, of:
   automatically sensing, in response to information provided by the dispenser, a type of the oral dispenser or a mode in which the dispenser is to operate so as to define sensed dispenser information;
   setting, as an alarm threshold, a minimum or maximum volume per unit time threshold, wherein the minimum or maximum volume per unit time threshold, respectively, is based on the sensed dispenser information;
   periodically determining a volume of fluids delivered by the pumping station through the dispenser; and
   if the volume so determined is less than the minimum volume per unit time threshold or greater than the maximum volume per unit time threshold, activating an alarm.

2. The method of claim 1 wherein the activating step comprises a step of providing a visual alarm indication.

3. The method of claim 1 wherein the activating step comprises a step of generating an audible alarm indication.

4. The method of claim 1 wherein the setting step comprises the steps of:
   determining whether a limit/time button on the pumping station is being depressed;
   if the limit/time button is being depressed, determining whether the alarm threshold reflects either minimum volume per unit time or maximum volume per unit time; and
   if the alarm threshold reflects the maximum volume per unit time:
      if an up key is depressed within a predetermined period of time after the limit/time button is initially depressed, incrementing the maximum volume per unit threshold by a predefined amount; and
      if a down key is depressed within the predetermined period of time, decrementing the maximum volume per unit threshold by the predefined amount; and
   if the alarm threshold reflects the minimum volume per unit time:
      if the up key is depressed within a predetermined period of time after the limit/time button is initially depressed, incrementing the minimum volume per unit threshold by the predefined amount; and
      if the down key is depressed within the predetermined period of time, decrementing the minimum volume per unit threshold by the predefined amount.

5. In a system for delivering fluids via an oral dispenser to a patient, the oral dispenser being connected through a fluid delivery tube to a pumping station, the method comprising the steps, performed at the pumping station, of:
   automatically sensing, in response to information provided by the dispenser, a type of the oral dispenser or a mode in which the dispenser is to operate so as to define sensed dispenser information; and setting, in response to the sensed dispenser information, pumping characteristics of a pump, contained within the pumping station, so as to controllably deliver the fluid to the patient in a predefined manner appropriate to the dispenser.

6. The method in claim 5 further comprising the steps of:

setting, as an alarm threshold, a minimum or maximum volume per unit time threshold, wherein the minimum or maximum volume per unit time threshold, respectively, is based on the sensed dispenser information;

periodically determining a volume of fluids delivered by the pumping station through the dispenser; and if the volume so determined is less than the minimum volume per unit time threshold or greater than the maximum volume per unit time threshold, activating an alarm.

7. The method of claim 6 wherein the activating step comprises a step of providing a visual alarm indication.

8. The method of claim 6 wherein the activating step comprises a step of generating an audible alarm indication.

9. The method of claim 6 wherein the setting step comprises the steps of:

determining whether a limit/time button on the pumping station is being depressed;

if the limit/time button is being depressed, determining whether the alarm threshold reflects either minimum volume per unit time or maximum volume per unit time; and if the alarm threshold reflects the maximum volume per unit time:

if an up key is depressed within a predetermined period of time after the limit/time button is initially depressed, incrementing the maximum volume per unit threshold by a predefined amount; and if a down key is depressed within the predetermined period of time, decrementing the maximum volume per unit threshold by the predefined amount; and if the alarm threshold reflects the minimum volume per unit time:

if the up key is depressed within a predetermined period of time after the limit/time button is initially depressed, incrementing the minimum volume per unit threshold by the predefined amount; and if the down key is depressed within the predetermined period of time, decrementing the minimum volume per unit threshold by the predefined amount.

10. In a system for delivering fluids via an oral dispenser to a patient, the oral dispenser being connected through a fluid delivery tube to a pumping station wherein said oral dispenser and said fluid delivery tube have substantially equal internal fluid pressures, the method comprising the steps, performed at the pumping station, of:

automatically sensing a change in said fluid pressure in said fluid delivery tube so as to automatically determine a type of the oral dispenser or a mode in which the dispenser is to operate;

setting, as an alarm threshold, a minimum or maximum volume per unit time threshold, wherein the minimum or maximum volume per unit time threshold, respectively, is based on said change in fluid pressure in said fluid delivery tube;

periodically determining a volume of fluids delivered by the pumping station through the dispenser; and if the volume so determined is less than the minimum volume per unit time threshold or greater than the maximum volume per unit time threshold, activating an alarm.

11. In a system for delivering fluids via an oral dispenser to a patient, the oral dispenser being connected through a fluid delivery tube to a pumping station wherein said oral dispenser and said fluid delivery tube have substantially equal internal fluid pressures, the method comprising the steps, performed at the pumping station, of:

automatically sensing, in response to a change in said internal fluid pressure so as to automatically determine a type of the oral dispenser or a mode in which the dispenser is to operate; and setting, in response to said change in internal pressure, pumping characteristics of a pump, contained within the pumping station, so as to controllably deliver the fluid to the patient in a predefined manner appropriate to the dispenser.

* * * * *

UNITED STATES PATENT AND TRADEMARK OFFICE
CERTIFICATE OF CORRECTION

PATENT NO.    : 6,358,237 B1
DATED         : March 19, 2002
INVENTOR(S)   : Dorothy A. Paukovits et al.

It is certified that error appears in the above-identified patent and that said Letters Patent is hereby corrected as shown below:

<u>Title page,</u>
Item [75], Inventors, please insert after "representative" and before "Hummelstown"
-- Edward J. Paukovits, Jr. --

Signed and Sealed this

Twenty-fourth Day of June, 2003

JAMES E. ROGAN
*Director of the United States Patent and Trademark Office*